United States Patent [19]

Digenis et al.

[11] Patent Number: 4,643,991
[45] Date of Patent: Feb. 17, 1987

[54] PEPTIDE ELASTASE INHIBITORS AND METHODS

[75] Inventors: George A. Digenis; Bushra J. Agha, both of Lexington, Ky.; Kiyoshi Tsuji, Osaka, Japan

[73] Assignee: The University of Kentucky Research Foundation, Lexington, Ky.

[21] Appl. No.: 683,316

[22] Filed: Dec. 18, 1984

[51] Int. Cl.$^4$ .................. A61K 37/64; C07K 5/08
[52] U.S. Cl. ..................................... 514/18; 530/331
[58] Field of Search ............... 260/326.4; 424/274; 514/18; 530/331

[56] References Cited

U.S. PATENT DOCUMENTS 4,155,914  5/1979  Batz et al. .................. 260/326.4
4,248,883  2/1981  Sawayama et al. ............ 424/274

OTHER PUBLICATIONS

F. Conti et al, "Cyclols–Formation from Tripeptide Systems and Structure Assignment by Carbon–13 Nuclear Magnetic Resonance", *Int. J. Peptide Protein Res.* 5, 1973, 353–357.

K. Tsuji et al, "Peptidyl Carbamate Esters: A New Class of Specific Elastase Inhibitors", *Biochemical and Biophysical Research Communications*, vol. 122, No. 2, 1984, pp. 571–576.

Primary Examiner—Delbert R. Phillips
Attorney, Agent, or Firm—Lowe, Price, LeBlanc, Becker & Shur

[57] ABSTRACT

Compounds useful as inhibitors of the enzyme elastase are of the following general formula:

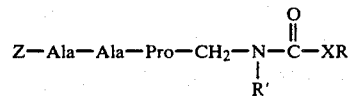

wherein Z is selected from the group consisting of R"O—Suc— where R" is lower alkyl of 1 to 3 carbon atoms and CF$_3$CO—; X is oxygen or sulfur; R' is selected from the group consisting of straight or secondary branch-chained alkyl of 1 to 4 carbon atoms, alkenyl of 2 to 3 carbon atoms, alkynyl of 2 to 4 carbon atoms, cycloalkyl of 3 to 6 carbon atoms, and benzyl, and R is selected from the group consisting of susbstituted or unsubstituted phenyl wherein the substituents are selected from the group consisting of nitro, and pentafluoro; benzyl, CH$_2$CF$_2$CF$_2$CF$_3$, 1-lower alkyl tetrazolyl, 1-phenyltetrazolyl, 2-thioxo-3-thiazolidinyl-, pyridyl and benzothiazolyl, provided that when R is paranitrophenyl, R' is other than tertiary-butyl, benzyl or cyclohexyl, and when X is sulfur, R is other than benzyl.

30 Claims, No Drawings

PEPTIDE ELASTASE INHIBITORS AND METHODS

FIELD OF THE INVENTION

This invention relates to inhibitors of the enzyme elastase and more particularly relates to the use of certain novel peptides containing the carbamate functionality which are active-site directed inhibitors of the enzyme elastase.

BACKGROUND OF THE INVENTION

Proteinases from polymorphonuclear leukocytes and macrophages, especially elastases (human leukocyte elastase and cathepsin G), appear to be responsible for the chronic tissue destruction associated with inflammation, arthritis and emphysema. During infection or inflammation, the normal lung is protected from proteolytic digestion by the protease inhibitor, $\alpha_1$-antitrypsin. The protective mechanism appears to be nonoperative in individuals with an $\alpha_1$-antitrypsin deficiency due to genetic or other causes. Synthetic elastase inhibitors capable of replacing $\alpha_1$-antitrypsin therefore appear to be useful in the treatment of pulmonary emphysema and related diseases.

Several types of elastase inhibitors have been reported in the literature. These include peptide chloromethyl ketones as described in "Inhibition of Human Leukocyte Elastase by Peptide Chloromethyl Ketones", P. M. Tuhy and J. C. Powers, *FEBS Letters*, 50, 359–61 (1975); "Specificity of Porcine Pancreatic Elastase, Human Leukocyte Elastase and Cathepsin G. Inhibition with Peptide Chloromethyl Ketones", J. C. Powers, B. F. Gupton, A. D. Harley, N. Nishino and R. J. Whitley, *Biochem. Biophys. Acta.* 485, 156–66 (1977); azapeptides "Proteinase Inhibitors. 1. Inhibitors of Elastase", C. P. Dorn, M. Zimmerman, S. S. Yang, E. C. Yurewicz, B. M. Ashe, R. Frankshun and H. Jones, *J. Med. Chem.*, 20, 1464–68 (1977); "Reaction of Serine Proteases with Aza-amino Acid and Aza-peptide Derivatives", J. C. Powers and B. F. Gupton, *Meth. Enzymol.*, 46, 208–16 (1977); sulfonyl fluorides "Specificity and Reactivity of Human Leukocyte Elastase, Porcine Pancreatic Elastase, Human Granulocyte Cathepsin G, and Bovine Pancreatic Elastase, Human Granulocyte Cathepsin G, and Bovine Pancreatic Chymotrypsin with Arylsulfonyl Fluorides. Discovery of a new series of potent and specific irreversible Elastase Inhibitors", T. Yoshimura, L. N. Barker and J. C. Powers, *J. Biol. Chem.*, 257, 5077–84 (1982); heterocyclic acrylating agents "Inhibition of Elastase and Other Serine Proteases by Heterocyclic Acylating Agents", M. Zimmerman, H. Morman, D. Mulvey, H. Jones, R. Frankshun and B. M. Ashe, *J. Biol. Chem.*, 255, 9848–51 (1980); "Selective Inhibition of Human Leukocyte Elastase and Bovine $\alpha_1$-Chymotrypsin by Novel Heterocycles", B. M. Ashe, R. L. Clark, H. Jones and M. Zimmerman, *J. Biol. Chem.*, 256: 11603–6 (1981); imidazole N-carboxamides, W. C. Groutas, R. C. Badger, T. D. Ocain, D. Felker, J. Frankson and M. Theodorakis, *Biochem. Biophys. Res. Commun.*, 95, 1890 (1980); and p-nitrophenyl-N alkyl carbamates, "p-Nitrophenyl Carbamates as Active-Site-Specific Reagents for Serine Proteases", R. E. Scofield, R. P. Werner and F. Wold, *Biochemistry*, 16, 2492 (1977).

Although some peptide chloromethyl ketones have been shown to be effective in preventing elastase induced emphysema in animal models "Prevention of Elastase Induced Experimental Emphysema by Oral Administration of a Synthetic Elastase Inhibitor,", A. Janoff and R. Dearing, *Am. J. Respir. Dis.*, 121, 1025-3 (1980), there is considerable question whether such reactive agents could be used for treating emphysema in humans. This is not surprising since the alkylating moieties in these inhibitors might render them toxic when used on a continuous basis. To be suitable for human use, an enzyme inhibitor has to show a high degree of selectively and must have minimal toxic side effects. As a result, most drugs are molecules that reversibly bind to specific enzymes or receptor sites. Examples are the carbamate esters physostigmine and neostigmine which have been clinically used as inhibitors of acetyl choline esterases, A. G. Gilman, L. S. Goodman, and A. Gilman, "The pharmacological Basis of Therapeutics", p. 101, MacMillan Publishing Co. (1980).

There accordingly remains a need in the art for compounds which are specific and active-site directed inhibitors of the enzyme elastase which are not subject to the disadvantages of compounds known in the art for this purpose.

SUMMARY OF THE INVENTION

It is accordingly one object of the present invention to provide novel compounds which are inhibitors of the enzyme elastase.

A further object of the invention is to provide specific active-site directed inhibitors of the enzyme elastase which are substituted carbamates.

A still further object of the invention is to provide methods for the specific inhibition of porcine pancreatic elastase and human leukocyte elastase by substituted carbamate compounds without affecting the similar serine dependent proteases, bovine pancreatic trypsin and chymotrypsin.

An even further object of the invention is to provide pharmaceutical compositions useful in the specific inhibition of porcine pancreatic elastase, said compositions containing as the active and effective component, certain substituted and novel carbamate compounds.

Further objects and advantages of the present invention will become apparent as the description thereof proceeds.

In satisfaction of the foregoing objects and advantages, the present invention provides substituted carbmate compounds of the following formula:

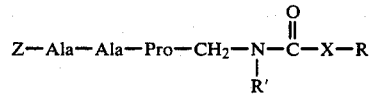

wherein Z is selected from the group consisting of R"O—Suc—where R" is lower alkyl of 1 to 3 carbon atoms, and $CF_3CO$—; X is oxygen or sulfur, R' is selected from the group consisting of straight or second-ary branch-chained alkenyl of 2 to 4 carbon atoms, alkynyl of 2 to 4 carbon atoms, alkyl of 1 to 4 carbon atoms, cycloalkyl of 3 to 6 carbon atoms, preferably cyclopropyl or cyclohexyl, and benzyl, and R is selected from the group consisting of substituted or unsubstituted phenyl wherein the substituents are selected from the group consisting of nitro, preferably p-nitro, and fluoro, preferably pentafluoro; benzyl, $CH_2CF_2CF_2CF_3$, 1-lower alkyl- and 1-phenyl tetrazolyl-, 2-thioxo-3-thiazolindinyl-, pyridyl, and benzothiazolyl, provided that when R is para-nitrophenyl, R' is other than tertiary-butyl, benzyl, or cyclohexyl, and when X is sulfur, R is other than benzyl.

The invention also provides elastase inhibiting pharmaceutical compositions containing these novel substituted carbamates as the active ingredients, methods for inhibiting the enzyme elastase in animals and humans, and methods for production of the compounds and compositions.

DESCRIPTION OF PREFERRED EMBODIMENTS

As pointed out above, the invention relates to certain novel substituted carbamate compounds, pharmaceutical compositions containing these compounds, and methods for use of these pharmaceutical compositions in the specific inhibition of porcine pancreatic elastase and human leukocyte elastase without affecting the similar serine dependent proteases, bovine pancreatic trypsin and chymotrypsin. It is known from the art that proteases from polymorphonuclear leukocytes and macrophages, especially elastases (human leukocyte HL elastase and cathepsin G) appear to be responsible for the chronic tissue destruction associated with inflammation, arthritis and emphysema. During infection or inflammation, the normal lung is protected from proteolytic digestion by the protease inhibitor, $\alpha_1$-anitrypsin. This protective mechanism appears to be non-operative in individuals with an $\alpha_1$-antitrypsin deficiency due to genetic or other causes. Synthetic elastase inhibitors capable of replacing $\alpha_1$-antitrypsin are therefore useful in the treatment of pulmonary emphysema and related diseases.

According to the present invention, a class of compounds containing carbamate functionality and oligopeptides have been found to be active-site directed inhibitors of elastase in animals and humans. This class of compounds therefore provide an opportunity to incorporate chemical moieties which will optimize the affinity of the inhibitor towards the enzyme, and transfer and acylating moiety to the active site of the enzyme. The nature of the acylating moiety could be varied to optimize the duration of enzymatic inactivation.

It is theorized that the mechanism of the invention takes advantage of the fact that the carbamate esters will react with proteases and esterases at the carbonyl carbon by losing the alkoxy portion and transferring the carbamylating moiety to the active site of the enzyme. Decylation will then lead to recovery of enzymatic activity.

The present invention provides a series of carbamate compounds which are active in accordance with the above proposals as elastase inhibitors. These compounds are carbamates substituted by oligopeptides and may generally be described by the following general formula:

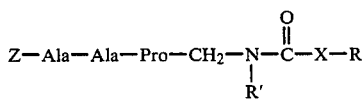

wherein Z is selected from the group consisting of R″O—Suc—where R″ is lower alkyl of 1 to 3 carbon atoms, and CF$_3$CO—; X is oxygen or sulfur, R' is selected from the group consisting of straight or secondary branched-chain alkyl of 1 to 4 carbon atoms, alkenyl of 1 to 4 carbon atoms, alkynyl of 2 to 4 carbon atoms, cycloalkyl of 3 to 6 carbon atoms, preferably cyclopropyl or cyclohexyl, and benzyl, and R is selected from the group consisting of substituted or unsubstituted phenyl wherein the substituents are selected from the group consisting of nitro, preferably p-nitro, and fluoro, preferably pentafluoro; benzyl, CH$_2$CF$_2$CF$_2$CF$_3$, 1-lower alkyl tetrazolyl-, 1-phenyltetrazolyl-, 2-thioxo-3-thiazolindyl, pyridyl, and benzothiazolyl, provided that when R is paranitrophenyl, R' is other than tertiary-butyl, benzyl or cyclohexyl, and when X is sulfur, R is other than benzyl.

In more preferred and detailed embodiments, the compounds of the invention may be described by the following general formulae A or B:

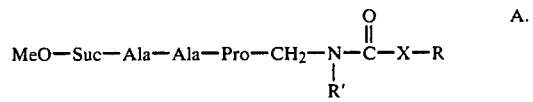

wherein X is oxygen or sulfur and R is selected from the group consisting of phenyl, fluorophenyl, nitrophenyl, 1-phenyltetrazolyl, 1-lower alkyl tetrazolyl, benzyl, 3-thiazolidinyl, pyridyl, and benzothiazolyl, and R' is straight or secondary branch chained alkyl of 2 to 4 carbons, alkenyl of 2 to 4 carbons, and alkynyl of 2 to 4 carbons, provided that when R is p-nitrophenyl, R' is other than tertiarybutyl, and when X is sulfur, R is other than benzyl; and

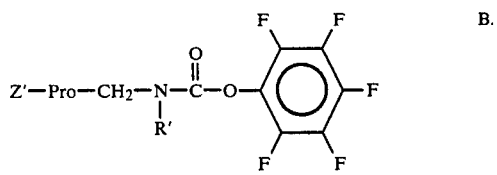

wherein Z is selected from the group consisting of MeO-Suc-Ala-Ala and CF$_3$CO-Ala-Ala, wherein R' is as defined above but is preferably isopropyl.

It will be noted from the description of the compounds that the peptidyl carbamates of this invention are those wherein the amino portion contains the oligopeptide and the peptide portion is so chosen as to increase the specificity of the carbamate ester for elastase.

In one embodiment, the compounds of the invention are prepared by a sequential series of reactions beginning with L-proline protected on the ring nitrogen with ultimate coupling to the peptide. In the first step, an N-protected proline, e.g., N-t-BOC-L-proline, is reacted with diazomethane to obtain the diazoketone followed by treatment with HCL to obtain the chloromethyl ketone protected L-proline. The chloromethyl ketone thus obtained is reacted with the appropriate amine H$_2$NR' to form the protected amine derivative. The amine is in turn reached with the appropriate chloroformate or thiochloroformate and deprotected by reaction with an acid such as HCl to provide the HCl salt. This compound is then coupled with Z-Ala-Ala by the mixed carbonic anhydride method to provide the compounds of the invention. The Z-Ala-Ala compounds are obtained by reaction of Ala-Ala with methyl succinic acid N-hydroxy succinimide ester when Z=R″O—Suc, e.g., MeOSuc. These Z-Ala-Ala intermediates may be prepared according to the following scheme:

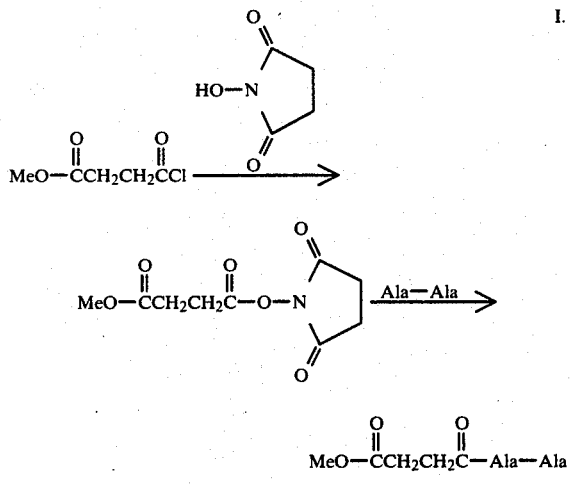

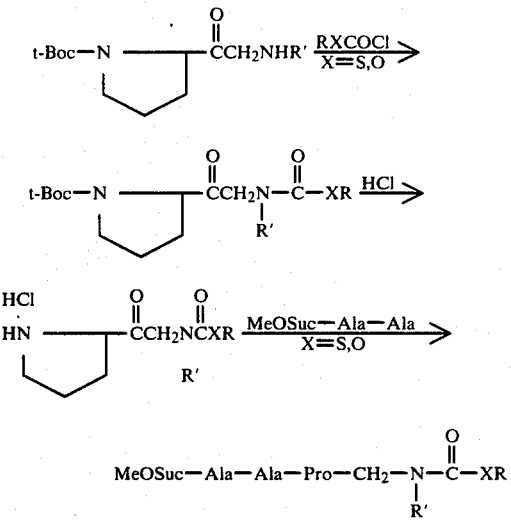

In conducting these reactions, the L-proline in the initial step is protected on the ring nitrogen by reaction with any suitable protective agent known to the art so that reaction will occur on the carboxylic acid portion of the molecule. Preferably, the nitrogen atom in the ring is protected with a known protective agent, such as t-BOC. For example, t-BOC-Pro is available commercially from Sigma Chemical Company, St. Louis, Mo. The protected proline is reacted with diazomethane by the method of Penke et al. (B. Penke, J. Czombos, L. Balaspiri, J. Peters and K. Kovacs, *Helv. Chim. Acta.*, 53, 1057 (1970). Thereafter, the resulting chloromethyl ketone is then reacted with the appropriate amine. This reaction is preferably conducted in a solvent solution, such as a lower alkyl alcohol, and preferably in the presence of an alkali metal iodide. The reactants are mixed under cool temperatures and then reacted at 50° to 75° C. to complete the reaction. The evolved HCl is neutralized, as with a sodium carbonate solution, and extracted. This intermediate is then reacted with the appropriate chloroformate or thiochloroformate and deprotected with hydrogen chloride to form the carbamate portion of the molecule. This molecule is then coupled with the peptide portion of the molecule to form the final product.

This reaction procedure may be illustrated as follows:

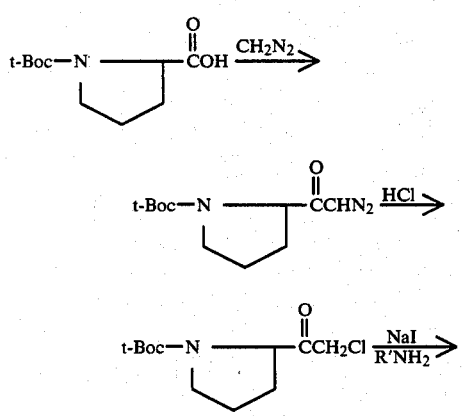

As pointed out above, the compounds of the invention may be employed as specific active site directed inhibitors of the enzyme, elastase. For this purpose, the compounds are preferably combined with a pharmaceutically acceptable carrier for administration by injection or in the oral form. Conventional adjuvants and carriers may be employed in combination with about 0.001 to 2.0 weight percent of the active compound. The compounds may be administered to animals or humans at dosage amounts ranging from about 1 mg/kg up to about 10 mg/kg, preferably an average amount of about 6 mg/kg.

The following examples illustrate preferred embodiments of the invention but the invention is not considered to be limited thereto. In the examples and throughout this specification, parts are by weight unless otherwise indicated.

In synthesis of the compounds of the invention, melting points were determined on a Thomas-Hoover Uni-Melt apparatus and are uncorrected. $^1$H NMR spectra were obtained using a Varian EM-360 (60 MH$_2$) or EM-390 (90 MH$_2$) spectrometer. Infrared (IR) spectra were recorded on a Perkin-Elmer 567 spectrophotometer. Microanalyses were performed by Atlantic Microlab, Inc., Atlanta, Ga. or by Micro Analysis, Inc., Wilmington, Del.

Reactions were routinely followed by thin layer chromatography (TLC) using Whatman MK6F silica gel plates. Spots were detected by UV (254 nm), iodine or HBr-Ninhydrin spraying. Column chromatography was carried out using Silica Gel 60 from E. Merck, Darmstadt, Germany. All compounds were identified by spectral data and elemental analysis.

EXAMPLE 1

Methyl Succinic Acid-N-hydroxysuccinimide Ester

To an ice-cooled solution of N-hydroxysuccinimide (1.15 g, 10 mmol) and methyl succinyl chloride (1.23 ml, 10 mmol) in ethyl acetate (50 ml) was added, dropwise, triethyl amine (1.4 ml, 10 mmol). The mixture was stirred at 4° C. for 10 min and at room temperature for 5 min. Filtration of insoluble materials, followed by the evaporation of the filtrate yielded pale yellow crystals. (2.1 g, 92%); m.p. 86°–88° C.

EXAMPLE 2

Methyl Succinyl-L-alanyl-L-alanine

Without further purification, the product from Example 1, (1.48 g, 6.46 mmol), was slowly added to a stirred solution of L-alanyl-L-alanine (862 mg, 5.38 mmol) and sodium bicarbonate (452 mg, 5.38 mmol) in water (5 ml) and acetone (5 ml). The mixture was stirred at room temperature for 4 h, and the acetone evaporated. The aqueous solution was washed with EtOAC (8 ml), acidified with citric acid (1.3 g), saturated with NaCl, and extracted four times with EtOAc (30 ml). The organic layers were washed with NaCl solution (3 ml) successively, combined, dried over anhydrous $MgSO_4$, and evaporated. The residue was washed with EtOAc to give colorless crystals of methyl succinyl-L-alanyl-L-alanine, (920 mg, 62%); m.p. 134°–135° C. NMR (DMSO-$d_6$)α 1.16 (d, 3H, J=7 Hz), 1.24 (d, 3H, J=7 Hz), 2.40 (t, 4H, J=7 Hz), 3.54 (S, 3H), 4.16 (quintet, 1H, J=7 Hz), 4.29 (quintet, 1H, J=7 Hz), 8.01 (d, 2H, J=7 Hz) ppm; IR (Nujol) 3280, 1735, 1690, 1630, 1540 $cm^{-1}$. Analysis calculated for $C_{11}H_{18}N_2O_6$: C, 48.17; H, 6.61; N, 10.21. Found: C, 48,05; H, 6.65; N, 10.17.

EXAMPLE 3

(N-t-Boc-L-prolyl)Diazomethane

This compound was prepared according to the method of Penke et al, *Helv. Chim. Acta.* 53, 1057 (1970).

EXAMPLE 4

(N-t-Boc-L-prolyl)Chloromethyl Ketone

Into an ice-cooled solution of the product of Example 3, (11.0 g) in ether (240 ml), HCl gas was introduced until the yellow solution turned colorless. The mixture was evaporated and purified by column chromatography (hexane/$CHCl_3$; 1:1) to give colorless crystals, (9.8 g, 51.7% from t-Boc-L-proline); m.p. 47°–49° C.; NMR ($CDCl_3$) & 1.47 (s, 9H), 1.8–2.2 (m, 4H), 3.4–3.8 (m, 2H), 4.36 (s, 2H), 4.4–4.8 (m, 1H); IR (Film) 1735, 1690 $cm^{-1}$. Anal Calcd for $C_{11}H_{18}ClNO_3$: C, 53.33; H, 732; n, 5.65; Cl, 14.31. Found: C, 53.46; H, 735; N, 5.56; Cl, 14.26.

EXAMPLE 5

N-(N'-t-Boc-L-prolyl)Methyl-N-Isopropylamine

To an ice-cooled solution of the product of Example 4, (3.0 g, 12.1 mmol) in 95% EtOH (30 ml), was added sodium iodide (1.95 g, 12.8 mmol) and isopropylamine (10.2 ml, 60 mmol). The mixture was shaken at 65° C. for 15 h and a saturated $NaHCO_3$ solution was added. The mixture was extracted into ether, evaporated and purified by column chromatography ($CHCl_3.CH_3OH$; 50:1) to give a brown oil, (1.84 g, 56%). NMR ($CDCl_3$) & 1.12 (d, 6H, J=6 Hz), 1.50 (s, 9H), 1.8–2.2 (m, 4H), 2.5–3.1 (m, 3H), 3.4–3.8 (m, 3H), 4.3–4.6 (m, 1H), IR (Film) 3330 (br), 1695 (br) $cm^{-1}$.

EXAMPLE 6 p-Nitrophenyl N-(N'-t-Boc-L-prolyl)Methyl-N-Isopropylcarbamate

A solution of p-nitrophenyl chloroformate (0.88 g, 4.34 mmol) in dry THF (10 ml) was added dropwise to a solution of the product of Example 5, 10.98 g, 3.36 mmol) and triethylamine (0.604 ml, 4.34 mmol) in THF at 5° C. The mixture was stirred at 5° C. for 2 h and filtered. The filtrate was evaporated and purified by column chromatography ($CHCl_3$/EtOAc; 100:1) to give a yellow oil (1.28 g, 81%). NMR ($CDCl_3$) & 1.0–1.3 (m, 6H), 1.3–1.5 (m, 9H), 1.7–2.2 (m, 4H), 3.3–3.7 (m, 2H), 4.0–4.7 (m, 4H), 7.1–7.4 (m, 2H), 8.1–8.4 (m, 2H); IR (Film) 1690–1740, 1590, 1520 $cm^{-1}$.

EXAMPLE 7

Phenyl N-(N'-t-Boc-L-Prolyl)Methyl-N-Isopropyl Carbamate

This compound was prepared using the procedure of Example 6 and the product of Example 5 as starting material, Yield, 95%; NMR ($CDCl_3$) & 1.1–1.4 (m, 6H), 1.47 (s, 9H), 1.7–2.1 (m, 4H), 3.4–3.7 (m, 2H), 3.8–4.6 (m, 4H), 7.0–7.5 (m, 5H); IR (Film) 1680–1750, 1595 $cm^{-1}$.

EXAMPLE 8 p-Nitrophenyl N-(L-Prolymethyl)-N-Isopropyl Carbamate Hydrochloride

A mixture of the product of Example 6 (1.65 mmol) in formic acid (5 ml) and 1N solution hydrogen chloride in THF (2 ml) was stirred at room temperature for 1 h. The mixture was evaporated and the oil obtained was triturated with $Et_2O$ to give the desired compound as crystals. Yield 68.8%; mp 190°–193° C. (dec); NMR 9DMSO-$d_6$) α 1.14 (d, 6H, J- 6 Hz), 1.6–2.2 (m, 4H), 3.1–4.8 (m, 6H), 7.52 (d, 2H, j-9 Hz), 8.48 (d, 2H, J-9 Hz); IR (Nujol) 1740, 1725, 1615, 1595, 1520 $cm^{-1}$. Anal. calcd for $C_{16}H_{22}ClN_3O_5$: C, 51.69; H, 5.96; N, 11.30; Cl, 9.53. Found: C, 51.52; H, 5.98; N, 11.21; Cl, 9.55.

EXAMPLE 9

Phenyl N-(L-Prolylmethyl)-N-Isopropyl Carbamate Hydrochloride

This compound was prepared using the procedure of Example 8 but the product of Example 7 as starting material. Yield, 58%; m.p. 207°–208° C. (dec); NMR (DMSO-$d_6$) & 1.0–1.4 (m, 6H), 1.7–2.2 (m, 4H), 3.0–3.7 (m, 2H), 4.1–4.9 (m, 4H), 7.1–7.7 (m, 5H); IR (Nujol) 1750, 1725, 1600, 1550 $cm^{-1}$. Anal. Calcd for $C_{16}H_{23}ClN_2O_3$: C, 58.80; H, 7.09; N, 8.57; Cl, 10.85. Found: C, 58.57; H, 7.13; N, 8.54; Cl, 10.92.

EXAMPLE 10 p-Nitrophenyl N-(Methy Succinyl-L-Alanyl-L-Alanyl-L-Prolymethyl)-N-Isopropyl Carbamate To a stirred mixture of methy/succinyl-L-alanyl-L-alanine from example 2 (213 mg, 0.778 mmol) and N-methyl morpholine (86 ul, 0.778 mmol) in THF (2.5 ml) at −15° to −30° C. was added, dropwise, a solution of isobutyl/chloroformate (101 ul, 0.778 mmol) in THF (1 ml), and the mixture stirred for 30 min at the same temperature. A solution of the product from Example 8, (0.779 mmol), N-methyl morpholine (0.778 mmol) and bis (trimethylsilyl) acetamide (1 ml in THF (3 ml) was then added dropwise to the above mixture at −50° C. The reaction mixture obtained was warmed up gradually stirred at room temperature overnight, diluted with $CHCl_3$ (10 ml), successively washed with 10% citric acid, and 4% $NaHCO_3$ solution and evaporated. The resulting oil was purified by column chromatography ($CHCl_3$ MeOH, 50:1) to give crystals. Yield, 82%; m.p. 153°–163° C.; NMR ($CDCl_3$) & 1.0–1.5 (m, 12H), 1.8–2.4 (m, 4H), 2.4–2.9 (m, 4H), 3.5–4.0 (m, 2H), 3.83 (s, 3H), 4.2–5.0 (m, 6H), 6.5–7.7 (m, 4H), 8.46 (d, 2H, J=7 Hz); IR (Nujol) 3350, 1737, 1720, 1688, 1655, 1645, 1525 cm$^{-1}$. Anal Calcd for C$_{27}$H$_{37}$N$_5$O$_{10}$: C, 54.82; H, 6.30; N, 11.84. Found: C, 54.60; H, 6.34, N, 11.73.

EXAMPLE 11

Phenyl N-(Methyl Succinyl-L-Alanyl-L-Alanyl-L-Prolyl Methyl)-N-Isopropyl Carbamate This compound was prepared using the procedure of Example 10 and the product of Example 9 as starting material. Yield, 67%; m.p. 60°–65° C.; NMR (CDCl$_3$) & 0.7–1.4 (m, 12H), 1.7–2.2 (m, 4H), 2.3–2.8 (m, 4H), 3.77 (s, 3H), 3.1–3.40 (m, 2H), 4.0–4.8 (m, 6H), 6.1–7.6 (m, 7H); IR (Film) 3300–3500, 1730 (br), 1645 (br), 1530 (br) cm$^{-1}$. Anal. calcd for C$_{27}$H$_{38}$N$_4$O$_8$: C, 59.33; H, 7.01; N, 10.25. Found: C, 59.16; H, 7.06; N, 10.17

EXAMPLE 12

(N-t-Boc-L-prolyl) chloromethane

The title compound was prepared in the same manner as that of Example 4. (76.3% yield from N-Boc-proline).

EXAMPLE 13

N-(N'-t-Boc-L-prolyl)methyl-N-isopropylamine

To a solution of (N-t-Boc-L-prolyl)chloromethane (3.0 g, 0.0121 mol) in ether (40 ml) at 5° C. was added isopropylamine (12 ml). The solution was stirred overnight in an ice bath and allowed to come to room temperature. Precipitated isopropylamine hydrochloride was filtered off and washed with ether. The filtrate was evaporated in vacuo to give an oil. The oil was purified by column chromatography (silica gel 45 g, solvent 2% MeOH-CHCl$_3$) to give 2.16 g of the product as an oil. NMR (&, CDCl$_3$), 1.12 (6H, d, J=6 Hz), 1.50 (9H, s), 1.8–2.2 (4H, m), 2.83 (1H, m), 3.3–3.9 (5H, m), 4.30 (1H, m) ppm; IR (Film) 3330 (br), 1690 cm$^{-1}$.

EXAMPLE 14

1-Methyl-5-tetrazolyl thiochloroformate

A solution of triethylamine (0.647 ml, 4.64 mmol) in THF (2 ml) was added dropwise to a mixture of 1-methyl-5-mercaptotetrazole (450 mg, 3.87 mmol) in the THF (5 ml) and 12.5% phosgene in benzene (4.7 ml, 6 mmol) at 0°–5° C. The mixture was stirred at 0°–5° C. for 30 min and at room temperature for 2 h, followed by filtration of the mixture. The filtrate obtained was evaporated go give 0.62 g (89.7%) of pale brown crystals of the title compound NMR (CDCl$_3$) & 4.23 (S, 3H), IR (Film) 1770 cm$^{-1}$.

EXAMPLE 15 1-Methyl-5-tetrazolyl N-(N'-t-Boc-L-prolyl)methyl-N-isopropylthiocarbamate To a solution of the product of Example 13 (1.95 g, 7.2 mmol) and triethylamine (1.30 ml, 9.36 mmol) in THF (15 ml) at 5° C. was added a suspension of 1-methyl-5-tetrazolyl thiochloroformate from Example 15, (1.67 g, 9.36 mmol) in THF (10 ml) over 4 min, and the mixture was stirred for 1 hour at 5° C. CHCl$_3$. The organic layer was dried over anhydrous MgSO$_4$ and evaporated in vacuo to give an oil. The oil was purified by column chromatography (silica gel 40 g) using CHCl$_3$ as an eluent to give 1.86 g of the product as an oil, 74% yield. The oil was crystallized from ethyl acetate-hexane mp 145°–150° C. NMR (&, CDCl$_3$) 1.30 (6H, d, J=6 Hz), 1.46 (9H, s), 1.8–2.2 (4H, m), 3.4–3.7 (2H, m), 4.10 (3H, s), 4.0–4.6 (4H, m) ppm IR (Film) 1735, 1685, 1670 cm$^{-1}$. Anal. Calcd for C$_{17}$H$_{28}$N$_6$O$_4$S: C, 49.50; H, 6.84; N, 20.37. Found: C, 49.65; H, 6.87; N, 20.30.

EXAMPLE 16

1-Methyl-5-tetrazolyl N-(L-prolylmethyl)-N-isopropylthio-carbamate Hydrochloride The title compound was prepared by the same method as that of Example 8 (52% yield).

EXAMPLE 17

1-Methyl-5-tetrazolyl N-(methyl succinyl-L-alanyl-L-alanyl-L-prolylmethyl)-N-isopropylthiocarbamate The title compound was prepared by the same method as that of Example 10. The obtained oil was crystallized from ethyl acetate-hexane, 21% yield, mp 110°–113° C. NMR (&, CDCl$_3$), 0.9–1.5 (12H, m), 1.8–2.2 (4H, m), 2.4–2.8 (4H, m), 3.5–3.8 (2H, m), 3.76 (3H, s), 4.10 (3H, s), 4.0–4.9 (6H, m), 6.56 (1H, brd, J-8 Hz), 7.20 (1H, brd, J=8 Hz), ppm. IR (Film); 3300, 1735, 1680–1640, 1520 cm$^{-1}$. Anal. Calcd. for C$_{23}$H$_{36}$N$_8$O$_7$S: C, 48.58; H, 6.38; N, 1970. Found: C, 48.41; H, 6.43; N, 19.58.

EXAMPLE 18

N-(N'-t-Boc-L-prolyl)methyl-N-cyclopropylamine

The title compound was prepared in a similar manner to Example 13 and obtained as an oil, 52.4% yield. NMR (&, CDCl$_3$) 0.33 (4H, m), 1.46 (9H, s), 2.0–2.3 (6H, m), 3.3–3.9 (4H, m), 4.40 (1H, m) ppm, IR (Film) 3260, 1720, 1680, 1400, 1160 cm$^{-1}$.

EXAMPLE 19

1-Methyl-5-tetraazolyl N-(N'-t-Boc-L-prolyl)methyl-N-cyclopropyl thiocarbamate The title compound was prepared in a similar manner to Example 15 as a powder, 30% yield. m p 144°–148° C. NMR (&, CDCl$_3$); 1.00 (4H, m), 1.46 (9H, s), 1.7–2.3 (4H, m), 2.96 (1H, m), 3.53 (2H, m), 4.06 (3H, s), 4.30 (3H, m) ppm. IR (Film) 1730, 1680, 1480, 1400 cm$^{-1}$. Anal. Calcd. for C$_{17}$H$_{26}$N$_6$O$_4$S: C, 49.75; H, 6.34; N, 20.48. Found: C, 49.49; H, 6.39; N, 20.34.

EXAMPLE 20

1-Methyl-5-tetrazolyl N-(L-prolylmethyl)-N-cyclopropylthiocarbamate Hydrochloride The compound of Example 39 (0.82 g, 2 mmol) was dissolved in ethyl acetate (30 ml). HCl gas was passed through the solution at room temperature for 5 minutes. After evaporation of the solvent, the residue was triturated with ether to give a powder 80% yield, mp 144°–148° C. NMR (&, DMSO-d$_6$): 1.00 (4H, m), 1.5–2.0 (4H, m), 3.20 (3H, m), 4.00 (1H, m), 4.07 (3H, s), 460 (2H, m) ppm. IR (Nujol) 1725 1670, 1260 cm$^{-1}$. Anal. Calcd. for C$_{12}$H$_{19}$ClN$_6$O$_2$S: C, 41.78; H, 5.48; N, 24.24; S, 9.23. Found: C, 41.60; H, 5.55; N, 24.17; S, 10.32.

EXAMPLE 21

1-Methyl-5-tetrazolyl N-(methyl succinyl-L-alanyl-L-alanyl-L-prolylmethyl)-N-cyclopropylthiocarbamate The title compound was prepared in a manner similar to Example 17. The product powder was obtained in 60.8% yield, mp 107°–109° C. NMR (&, CDCl$_3$) 1.00 (4H, m), 1.36 (6H, d, J=6 Hz), 1.8–2.4 (4H, m), 2.63 (4H, m), 3.0 (1H, m), 3.66 (2H, m), 3.73 (3H, s), 4.08 (3H, s), 4.3–4.9 (5H, m) ppm. IR (CHCl$_3$) 3300–3400, 1730, 1710, 1680, 1510 cm$^{-1}$. Anal. Calcd. for C$_{23}$H$_{34}$N$_8$O$_7$S: C, 48.76; H, 6.05; N, 19.77. Found C, 48.56; H, 6.07; N, 19.57.

EXAMPLE 22

N-(N-t-Boc-L-prolyl)methyl-N-propylamine

The title compound was prepared in a similar manner to Example 13 as an oil, 54% yield. NMR (&, CDCl$_3$) 0.90 (3H, t, J=7 Hz), 1.43 (9H, s), 1.6–2.3 (6H, m), 2.67 (2H, t, J=7 Hz), 3.3–3.7 (4H, m), 4.33 (1H, m) ppm. IR (Film) 3300, 1710, 1690, 1380 cm$^{-1}$.

EXAMPLE 23

1-Methyl-5-tetrazolyl N-(N'-t-Boc-L-prolyl)methyl-N-propyl thiocarbamate

The title compound was prepared in a similar way to Example 15 to give crystals, 23.5% yield. mp 112°–114° C. NMR (&, CDCl$_3$) 1.00 (3H, t, J=7 Hz), 14.6 (oH, s), 1.6–2.3 (6H, m), 3.2–3.7 (4H, m), 4.10 (3H, s), 4.30 (3H, m) ppm. IR (Film) 1730, 1680, 1380, 1160 cm$^{-1}$. Anal. Calcd. for C$_{17}$H$_{28}$N$_6$O$_4$S: C, 49.51; H, 6.79; N, 20.38. Found: C, 49.23; H, 6.84; N, 20.30.

EXAMPLE 24

1-Methyl-5-tetrazolyl N-(L-prolylmethyl)-N-propylthio carbamate Hydrochloride

The title compound was prepared in a similar manner to Example 20, 84% yield, m p 107°–112° C. NMR (&, DMSO-d$_6$) 1.0 (3H, m), 1.2–2.0 (6H, m), 3.0 (2H, m), 4.07 (3H, s), 4.25–5.0 (5H, m) ppm. IR (Film) 3350, 1740, 1680 cm$^{-1}$.

EXAMPLE 25

1-Methyl-5-tetrazolyl N-(methyl succinyl-L-alanyl-L-alanyl-L-prolylmethyl)-N-propylthiocarbamate The title compound was prepared in a similar manner to Example 17, mp, 138°–140° C. 22.3% yield. IR (Film) 3300, 1735, 1650, 1530, 1170 cm$^{-1}$. NMR (&, CDCl$_3$) 1.00 (3H, br, t, J=7 Hz), 1.40 (6H, d, J=7 Hz) 1.2–1.8 (2H, m), 2.07 (4H, m), 2.66 (4H, m), 3.50 (2H, m), 3.70 (3H, s), 4.10 (3H, s), 4.2–5.0 (5H, m), 6.9 (1H, m), 7.4 (1H, m) ppm. Anal. calcd. for C$_{23}$H$_{36}$N$_8$O$_7$: C, 48.58; H, 6.38; N, 19.71. Found: C, 48.37; H, 6.38; N, 19.64.

EXAMPLE 26 p-Nitrophenyl N-(N'-t-Boc-L-prolyl)methyl-N-propylcarbamate

The title compound was prepared in the same way as that of Example 6 to recover an oil, 51.7% yield. NMR (&, CDCl$_3$) 0.93 (3H, br, t, J=7.5 Hz), 1.46 (9H, s), 1.5–2.5 (6H, m), 3.50 (4H, m), 4.30 (3H, m), 7.40 (2H, m), 8.30 (2H, m) ppm. IR (Film) 1740, 1700, 1670, 1610 cm$^{-1}$.

EXAMPLE 27

P-Nitrophenyl N-(L-prolylmethyl)-N-propylcarbamate Hydrochloride

The title compound was prepared in the same manner as previous Example 8. The compound of Example 26 (0.72 g, 1.65 mmol) was dissolved in a mixture of formic acid (10 ml) and 1N HCl in THF (10 ml). The solution was stirred at room temperature for 3 hours. Evaporation of the solvent gave a residue which was triturated with ether to give a powder. The powder was collected and washed with ether to give 0.49 g of the product. 79.8% yield. m p 155°–160° C. NMR (&, DMSO-d$_6$) 0.9 (3H, br, t, J=9 Hz), 1.1–2.2 (6H, m), 3.0–3.7 (4H, m), 4.3–4.8 (3H, m), 7.46 (2H, d, J=9 Hz), 8.37 (2H, d, J=9 Hz) ppm. IR (Nujol) 3400, 1720, 1610, 1590, 1520 cm$^{-1}$.

EXAMPLE 28

P-Nitrophenyl N-(methyl succinyl-L-alanyl-L-alanyl-L-prolylmethyl) N-propylcarbamate The title compound was prepared in the same manner as that of Example 10. 20.1% yield, m p 158°–161° C. NMR (&, CDCl$_3$) 0.96 (3H, m), 1.36 (6H, br, d, J=6.5 Hz), 1.5–2.3 (6H, m), 2.63 (4H, br, s), 3.2–4.0 (4H, m), 3.70 (3H, s), 4.2–5.0 (5H, m), 7.0 (1H, br, d, J=6.5 Hz), 7.1–7.63H, m), 8.30 (2H, br, d, J=9 Hz) ppm. IR (film) 3320, 1740, 1650, 1580, 1550 cm$^{-1}$.

EXAMPLE 29

P-Nitrophenyl N-(N'-t-Boc-L-prolyl)methyl-N-cyclopropylcarbamate

The title compound was prepared in the same way as that of Example 6 as an oil. 45% yield, NMR (&, CDCl$_3$) 0.86 (4H, m), 1.50 (9H, s), 1.7–2.5 (4H, m), 3.0 (1H, m), 3.56 (2H, m), 4.40 (3H, m), 7.43 (2H, brd, J=9 Hz), 8.33 (2H, br, d, J=9 Hz) ppm IR (film) 1740, 1720, 1700, 1610, 1590, 1390, 1210 cm$^{-1}$.

EXAMPLE 30

P-Nitrophenyl N-(L-prolylmethyl)-N-cyclopropylcarbamate hydrochloride)

HCl gas was passed through a solution of the product of Example 29 (1.3 g, 3.0 mmol) in ether (40 ml) for 6 min at room temperature. Precipitated amine salts were collected and washed with ether to give the product (0.7 g), 63% yield. m p 150° C. (dec). NMR (&, CDCl$_3$), 0.81 (4H, m), 1.7–2.3 (4H, m), 2.90 (1H, m) 3.23 (2H, m), 4.60 (3H, m), 7.46 (2H, brd, J=9 Hz), 8.36 (2H, d, J=9 Hz). Anal. Calcd for C$_{16}$H$_{20}$ClN$_3$O$_5$: C, 51.96; H, 5.44; N, 11.36. Found, C, 51.72; H, 5.48; N, 11.30.

EXAMPLE 31

P-Nitrophenyl N-(methyl succinyl-L-alanyl-L-analyl-L-prolylmethyl)-N-cyclopropylcarbamate The title compound was prepared in the same manner as Example 10 and was obtained as a powder, 61% yield. m p 154°–158° C. IR (film) 3340, 1740, 1690, 1655, 1640, 1590, 1520 cm$^{-1}$. NMR (&, CDCl$_3$) 0.83 (4H, m), 1.40 (6H, d, J=7 Hz), 1.8–2.3 (4H, m), 2.60 (4H, m), 3.0 (1H, m), 3.60 (2H, m), 3.70 (3H, s), 4.2–5.0 (5H, m), 6.38 (1H, br, d, J=8 Hz), 7.03 (1H, br, t, J=8 Hz), 7.36 (2H, d, J=9 Hz), 8.30 (2H, d, J=9 Hz). Anal. Calcd. for C$_{27}$H$_{35}$N$_{5}$O$_{10}$: C, 55.00, H, 5.98; N, 11.88. Found C, 54.80; H, 5.99; N, 11.76.

EXAMPLE 32

N-(N'-t-Boc-L-prolyl)methyl-N-butylamine

To a solution of the product of Example 12 (2.8 g, 0.0113 mol) in ether (70 ml) at 5° C. was added n-butylamine (8.2 ml 0.0831 mol). The solution was stirred at 5° C. for 5 hours. Precipitated salts were filtered and washed with ether. The filtrate was evaporated in vacuo to give an oil. The oil was purified by column chromatography (silica gel 15 g, solvent 2% MeOH-CHCl$_3$) to give 3.2 g of the product as an oil. IR (Film) 3300, 1690, 1380 cm$^{-1}$. NMR (&, CDCl$_3$) 1.0 (3H, m), 1.50 (9H, s), 1.2–1.8 (4H, m), 1.8–2.2 (4H, m), 2.60 (2H, m), 3.1–3.9 (5H, m), 4.33 (1H, m).

EXAMPLE 33

1-Methyl-5-tetrazolyl N-(N'-t-Boc-L-prolyl)methyl-N-butyl thiocarbamate

The title compound was prepared in a manner similar to Example 15, 35.1% yield, mp 125°–128° C. IR (Nujol), 1735, 1670, 1170, 1120 cm$^{-1}$, NMR (&, CDCl$_3$), 0.96 (3H, brt, J=5 Hz), 1.46 (9H, s), 1.2–1.8 (4H, m), 2.0 (4H, m), 3.2–3.7 (4H, m), 4.07 (3H, s), 4.2–4.6 (3H, m) ppm. Anal. Calcd. for C$_{18}$H$_{30}$N$_{6}$O$_{4}$S. C, 50.69; H, 7.09; N, 19.70. Found: C, 50.75; H, 7.14; N, 19.66.

EXAMPLE 34

1-Methyl-5-tetrazolyl N-(L-prolylmethyl)-N-butylthiolcarbamate Hydrochloride

The title compound was prepared in a similar manner to Example 20, 91.9% yield, m p 120°–129° C. IR (Nujol) 3350, 1735, 1665, 1560, 1200 cm$^{-1}$. NMR (&, DMSO-d$_6$) 0.96 (3H, m), 1.2–2.3 (8H, m), 3.0–3.6 (4H, m), 4.06 (3H, s), 4.4–5.0 (3H, m). Anal. Cacld. for C$_{13}$H$_{23}$ClN$_{6}$O$_{2}$S; C, 43.03; H, 6.39. Found C, 43.10; H, 6.62.

EXAMPLE 35

1-Methyl-5-tetrazolyl N-(methyl succinyl-L-alanyl-L-alanyl-L-prolymethyl)-N-butylthiocarbamate To a solution of the product of Example 2, (0.428 g, 0.00173 mol) and N-methyl morpholine (0.175 g, 0.00173 mol) in THF (3 ml) at −15° C. was added a solution of isobutyl chloroformate (0.236 g, 0.00173 mol) in THF (1.6 ml). The mixture was stirred at −15° C. for 10 minutes. To the mixture at −15° C. was added a solution of the product of Example 34, (0.57 g, 0.00157 mol) and N-methyl-morpholine (0.159 g) in CH$_3$CN (5 ml). The mixture was stirred at 5° C. for 1.5 hours and stored at 5° C. overnight. The reaction mixture was diluted with CHCl$_3$, washed with 10% aq. citric acid, water and saturated NaCl solution, and dried over anhydrous MgSO$_4$. Evaporation of the solvents gave an oily residue which was purified by column chromatography (silica gel 16 g, solvent: 2% MeOH-CHCl$_3$) to give 0.37 g of the product as an oil. The oil was crystallized from ethyl acetate-hexane to give 0.27 g of the product, mp 140°–145° C. 29.5% yield. IR (Nujol) 3340, 1730, 1690, 1655, 1630, 1535 cm$^{-1}$. NMR (& CDCl$_3$) 1.00 (3H, m), 1.2–1.8 (4H, m), 1.37 (6H, d, J=7 Hz), 2.07 (4H, m), 2.63 (4H, m), 3.3–3.9 (4H, m), 3.73 (3H, s), 4.10 (3H, s), 4.2–5.0 (5H, m), 6.50 (1H, br, d, J=7 Hz), 7.10 (1H, br, d, J=7 Hz) ppm. Anal Calcd. for C$_{24}$H$_{38}$N$_{8}$O$_{7}$S: C, 49.47; H, 6.57; N, 19.23. Found=C, 49.52; H, 6.58; N, 19.08.

EXAMPLE 36

1-Phenyl-5-tetrazolyl N-(N'-t-Boc-L-prolyl)methyl-N-isopropylthiocarbamate

The title compound was prepared in a similar manner as that of Example 15 as an oil, 73.8% yield. IR (Film) 1735, 1690, 1590, 1495, 1400 cm$^{-1}$. NMR (&, CDCl$_3$), 1.17 (6H, d, J=7 Hz), 1.47 (9H, s), 1.95 (4H, m), 3.46 (2H, m), 3.9–4.6 (4H, m), 7.70 (5H, s).

EXAMPLE 37

1-Phenyl-5-tetrazolyl N-(L-prolylmethyl)-N-isopropylthiocarbamate Hydrochloride

The title compound was prepared in a similar manner to Example 20 as an amorphous powder 46.2% yield. IR (Nujol) 3400, 1760, 1730, 1670, 1590 cm$^{-1}$. NMR (&, DMSO-d$_6$) 1.13 (6H, m), 2.0 (4H, m), 3.30 (2H, m), 3.8–4.8 (4H, m), 7.7–8.0 (5H, m) ppm.

EXAMPLE 38

1-Phenyl-5-tetrazolyl N-(methyl succinyl-L-alanyl-L-alanyl-L-prolylmethyl)-N-isopropylthiolcarbamate The title compound was prepared in a similar manner to Example 35, 44.0% yield, mp 103°–108° C. IR (Nujol) 3340, 1735, 1680, 1655, 1530 cm$^{-1}$. NMR (&, CDCl$_3$), 0.8–1.7 (12H, m), 2.03 (4H, m), 2.60 (4H, m), 3.66 (2H, m), 7.60 (5H, s) ppm. Anal. Calcd. for C$_{28}$H$_{38}$N$_{8}$O$_{7}$S: C, 53.32; H, 6.07; N, 17.77. Found: C, 53.17; L H, 6.15; N, 17.68.

EXAMPLE 39

N-(N'-t-Boc-L-prolyl)methyl-N-allylamine

The title compound was prepared in a similar manner as that of Example 13 as an oil, 55.9% yield IR (Film) 3320, 1700, 1400, 1160 cm$^{-1}$. NMR (&, CDCl$_3$) 1.46 (9H, s), 2.00 (4H, m), 3.30 (2H, d, J=5.5 Hz), 3.4–3.8 (4H, m), 4.40 (1H, m), 5.0–5.4 (2H, m), 5.5–6.3 (1H, m) ppm.

EXAMPLE 40

1-Methyl-5-tetrazolyl N-(N'-t-Boc-L-prolyl)methyl-N-allylthiocarbamate

The tile compound was prepared in a similar manner as that of Example 15, as a powder, 39.5% yield, mp 124°–126° C. IR (CHCl$_3$) 1735, 1685, 1160 cm$^{-1}$. NMR (&, CDCl$_3$): 1.47 (9H, s), 2.0 (4H, m), 3.50 (2H, m), 4.10 (3H, s), 4.0–4.6 (5H, m), 5.1–5.5 (2H, m), 5.6–6.4 (1H, m) ppm. Anal. Calcd for C$_{17}$H$_{26}$N$_{6}$O$_{4}$S C, 49.74, H, 6.38; N, 20.47 Found: C, 49.50; H, 6.45; N, 20.37.

EXAMPLE 41

1-Methyl-5-tetrazolyl N-(L-prolylmethyl)-N-allylthiocarbamate Hydrochloride

The title compound was prepared in a similar manner as Example 20 as a powder, 93.8% yield, NMR (&, DMSO-D$_6$), 1.90 (4H, m), 3.20 (2H, m), 4.07 (3H, s), 3.9–4.9 (5H, m), 5.0–5.6 (2H, m), 5.7–6.3 (1H, m) ppm.

EXAMPLE 42

1-Methyl-5-tetrazolyl N-(methyl succinyl-L-alanyl-L-alanyl-L-prolylmethyl)-N-allylthiocarbamate The title compound was prepared in a similar manner as Example 17 as a powder. 24.3% yield, mp 143°–145° C. IR (Film) 3340, 1735, 1660, 1530, 1450 cm$^{-1}$. NMR (&, CDCl$_3$), 1.40 (6H, d, J=Hz), 2.10 (4H, m), 2.66 (4H, m), 3.73 (3H, s), 3.6–3.8 (2H, m), 4.10 (3H, s), 4.1–5.0 (7H, m), 5.1–5.6 (2H, m), 5.6–6.3 (1H, m), 6.8 (1H, br, d, J=7 Hz), 7.20 (1H, m) ppm. Anal. Calc. for C$_{23}$H$_{34}$N$_8$O$_7$S: C, 48.75; H, 6.05; N, 19.78. Found C, 48.51, H, 6.08, N, 19.68.

EXAMPLE 43

N-(N'-t-Boc-L-prolyl)methyl-N-(2-methyl)proplyamine

The title compound was prepared in a similar manner as Example 13 as an oil, 69.75 yield. NMR (&, CDCl$_3$), 0.93 (6H, d, J=6 Hz), 1.46 (9H, s), 1.3–1.6 (1H, m), 2.0 (4H, m), 2.43 (2H, m), 3.3–4.3 (4H, m), 4.40 (1H, m) ppm. IR (Film) 3340, 1700, 1470, 1400 cm$^{-1}$.

EXAMPLE 44

P-Nitrophenyl N-(N'-t-Boc-L-prolyl)methyl-N-(2-methyl)lpropylcarbamate

The title compound was prepared in a similar manner as Example 6 as an oil, 93% yield. IR (Film) 1730, 1615, 1595, 1525 cm$^{-1}$. NMR (&, CDCL$_3$), 0.96 (6H, d, J=6 Hz), 1.43 (9H, s), 1.3–1.6 (1H, m), 2.0 (4H, m), 3.1–3.8 (4H, m), 4.1–4.6 (3H, m), 7.3 (2H, br, d, J=9 Hz), 8.33 (2H, d, J=8 Hz) ppm.

EXAMPLE 45

P-Nitrophenyl N-(L-prolylmethyl)-N-(2-methyl) propylcarbamate Hydrochloride

The title compound was prepared in a similar manner as that of Example 30 as a powder, 47% yield, mp 135°–149° C. IR (Nujol) 3500, 1740, 1710, 1615, 1595 cm$^{-1}$. NMR (&, DMSO-d$_6$), 0.95 (6H, d, J=6 Hz), 1.3–2.2 (7H, m), 3.0–3.6 (4H, m), 4.1–4.8 (3H, m), 7.43 (2H, br, d, dd, J=2, 9 Hz), 8.36 (2H, d, J=9 Hz) ppm.

EXAMPLE 46 p-Nitrophenyl N-(methyl succinyl-L-alanyl-L-alanyl-L-prolylmethyl)-N-(2-methyl)propylcarbamate The title compound was prepared in a similar manner as that of Example 10 as a powder, 57.7% yield mp 177°–179° C. IR (Nujol) 3350, 1735, 1695, 1660, 1635, 1595 cm$^{-1}$. NMR (&, CDCl$_3$): 0.96 (6H, d, J=7.5 Hz), ;b 1.35 (6H, d, J=7 hz), 1.5–2.0 (1H, m), 2.0 (4H, m), 2.60 (4H, m), 3.30 (2H, m), 3.70 (3H, s), 3.70 (2H, m), 4.1–5.0 (5H, m), 6.50 (1H, br, d, J=7 Hz), 7.10 (1H, m), 7.30 (2H, d, J=9 Hz), 8.30 (2H, d, J=9 Hz) ppm. Anal. Calcd. for C$_{28}$H$_{39}$N$_5$O$_{10}$: C, 55.53; H, 6.44; N, 11.57. Found: C, 55.29; H, 6.55; N, 11.46.

EXAMPLE 47

N-(N'-t-Boc-L-prolyl)methyl-N-phenylmethylamine

The title compound was prepared in a similar manner as Example 13 as an oil, 63.5% yield. IR (Film) 3310, 1700, 1605, 1585, 1400 cm$^{-1}$. NMR (&, CDCl$_3$), 1.43 (9H, s), 1.96 (4H, m), 3.3–4.0 (6H, m), 4.33 (1H, m), 7.36 (5H, s) ppm.

EXAMPLE 48

P-Nitrophenyl N-(N'-t-Boc-L-prolyl)methyl-N-phenylmethylcarbamate

The title compound was prepared in a similar manner as that of Example 6 as an oil, 56% yield. IR (CHCl$_3$): 1730, 1690, 1615, 1595, 1525 cm$^{-1}$. NMR (&, CDCl$_3$): 1.43 (9H, s), 1.7–2.3 (4H, m), 3.50 (2H, m), 4.0–5.0 (5H, m), 7.37 (7H, m), 8.33 (2H, d, J=0 Hz) ppm.

EXAMPLE 49

P-Nitrophenyl N-(L-prolylmethyl)-N-phenylmethylcarbamate Hydrochloride

The title compound was prepared in a similar manner as that of Example 30 was a powder. 38.4% yield mp 136°–142° C. IR (Nujol) 3400, 1730, 1670, 1590 cm$^{-1}$. NMR (&, DMSO-d$_6$), 2.00 (4H, m), 3.3 (2H, m), 4.2–5.0 (5H, m), 7.3–7.4 (7H, m), 8.33 (2H, d, J=9 Hz) ppm.

EXAMPLE 50

P-Nitrophenyl N-(methyl succinyl-L-alanyl-L-alanyl-L-prolylmethyl)-N-phenylmethylcarbamate The title compound was prepared in a similar manner as that of Example 10 as a powder, 39.6% yield mp 141°–143° C. IR (Nujol) 3340, 1730, 1690, 1660, 1630, 1520 cm$^{-1}$. NMR (&, CDCl$_3$), 1.2–1.8 (6H, m), 2.00 (4H, m), 3.70 (2H, m), 4.2–5.0 (7H, m), 6.46 (1H, m), 3.70 (3H, s), 3.70 (2H, m), 4.2–5.0 (7H, m). 6.46 (1H, br, d, J=7 Hz), 7.10 (1H, br, d, J=7 Hz), 7.3–7.6 (7H, m), 8.33 (2H, d, J=9 Hz) ppm. Anal. Calcd. for C$_{31}$H$_{37}$N$_5$O$_{10}$. C, 58.21; H, 5.79; N, 10.95. Found: C, 57.97; H, 5.86; N, 10.89.

EXAMPLE 51

N (N'-t-Boc-L-prolyl)methyl-N-cyclohexylamine

The title compound was prepared in a similar manner as that of Example 13 as an oil, 43.9% yield. IR (Film) 3320, 1690, 1390 cm$^{-1}$. NMR (&, CDCl$_3$), 0.9–2.5 (15H, m), 1.47 (9H, s), 3.3–3.9 (4H, m), 4.33 (1H, m), ppm.

EXAMPLE 52

P-Nitrophenyl N-(N'-t-Boc-L-prolyl)methyl-N-cyclohexylcarbamate)

The title compound was prepared in a similar manner as that of Example 6 as an oil, 80.1% yield IR (Film) 1725, 1690, 1612, 1590, 1520 cm$^{-1}$. NMR (&, CDCl$_3$), 0.9–2.3 (14H, m), 1.47 (9H, s), 3.3–4.0 (3H, m), 4.1–4.6 (3H, m), 7.13 (2H, dd, J=3.5, 9 Hz), 8.30 (2H, d, J=9 Hz) ppm.

EXAMPLE 53

P-Nitrophenyl N-(L-prolylmethyl)-N-cyclohexylcarbamate Hydrochloride

The title compound was prepared in a similar manner as that of Example 30 as a powder, 77.3% yield, mp 146°–158° C. IR (Nujol) 1720, 1612, 1595, 1515 cm$^{-1}$. NMR (&, DMSO-d$_6$) 1.1–2.6 (14H, m), 3.3–4.9 (6H, m), 1.47 (2H, dd, J=3.5, 9 Hz), 8.43 (2H, d, J=9 Hz) ppm.

EXAMPLE 54

P-Nitrophenyl N-(methyl succinyl-L-alanyl-L-alanyl-L-prolylmethyl)-N-cyclohexylcarbamate The title compound was prepared in a similar manner as that of Example 10 as a powder, 62.9% yield mp 150°–154° C. IR(Nujol) 3345, 1735, 1690, 1655, 1595 cm$^{-1}$. NMR(&, CDCl$_3$), 1.2–2.4(14H, m), 1.40(6H, d, J=7.5 Hz), 2.66(4H, m), 3.73(3H, s), 3.5–5.0(8H, m), 6.4 (1H, m), 7.0(1H, m), 7.4(2H, d, J=9 Hz), 8.33(2H, d, J=9 Hz). Anal. Calcd. for C$_{30}$H$_{41}$N$_5$O$_{10}$: C, 57.05; H, 6.49; N, 11.09. Found: C, 56.87; H, 6.54; N, 11.00

EXAMPLE 55

Pentafluorophenyl-N-(N'-t-Boc-L-prolyl methyl-N-isopropylcarbamate

This compound was prepared according to the procedure described in Example 6; NMR (CDCl$_3$) & 1.1–1.4 (m, 6H), 1.48 (S, 9H), 1.9–2.3 (m, 4H, 3.4–3.8 (m, 2H), 4.2–4.7 (m, 4H); IR (Film) 1750, 1690, 1515 cm$^{-1}$$^{-t}$.

EXAMPLE 56

Pentafluorophenyl-N-(L-prolylmethyl)-N-isopropyl carbamate hydrochloride

This compound was prepared according to the procedure described in Example 8: mp 189°–190° C.; NMR (DMSO-d$_6$) & 1.0–1.3 (m, 6H), 1.7–2.3 (m, 4H), 3.1–3.5 (m, 2H), 4.0–4.9 (M, 4H); IR (Nujol) 1750, 1515 cm$^{-1}$. Anal. calcd. for C$_{16}$H$_{18}$N$_2$ClF$_5$O$_3$: C, 46.11, H, 4.35; N, 6.72, Cl, 8.50. Found: C, 45.94; H, 4.38; N, 6.66; Cl, 8.67.

EXAMPLE 57

Pentafluorophenyl N-(methyl succinyl-L-analyl-L-alanyl-L-prolymethyl)-N-isopropyl-carbamate This compound was prepared according to the procedure described in Example 10: yield, 44%; mp 152°–154° C.; NRM (CDCl$_3$) & 1.0–1.5 (m, 12H), 1.8–2.3 (m, 4H), 2.5–2.8 (m, 4H), 3.4–4.0 (m, 2H), 3.75 (S, 3H), 4.0–5.0 (m, 6H), 6.2–7.4 (br, 2H), IR (Nujol) 3350, 1765, 1740, 1690, 1660, 1640, 1520 cm$^{-1}$. Anal. calcd for C$_{27}$H$_{33}$N$_4$F$_4$O$_8$: C, 50.94, H, 5.22; N, 8.80. Found: C, 50.85; H, 5.26; N, 8.78.

EXAMPLE 58

Heptafluorobutyl N-(N'-t-Boc-L-prolyl)methyl-N-isopropyl carbamate

This compound was prepared following the same procedure as in Example 6: NMR (CDCl$_3$) & 1.13 (d, 6H, J-7 Hz), 1.49 (S, 9H), 1.8–2.2 (m, 4H), 3.4–3.7 (m, 2H), 4.0–5.0 (m, 6H); IR (Film) 1690–1740 cm$^{-1}$.

EXAMPLE 59

Heptafluorobutyl N-(L-prolylmethyl)-N-isopropyl carbamate hydrochloride

This compound was prepared following the procedure in Example 8; mp 149°–150° C.; NMR (DMSO-d$_6$) & 1.11 (d, 6H, J-7 Hz), 1.7–2.3 (m, 4H), 3.0–3.4 (m, 2H), 3.9–5.2 (m, 4H), 4.40 (S, 2H), 9.7 (br, 2H); IR(Nujol) 3410, 1745, 1710 cm$^{-1}$. Anal. calcd for C$_{14}$H$_{20}$N$_2$ClF$_7$O$_3$: C$_l$ 38.86; H, 4.66; N, 6.47; Cl, 8.19. Found: C, 38.58; H, 4.68; N, 6.43; Cl, 8.20.

EXAMPLE 60

Heptafluorobutyl N-(methyl succinyl-L-alanyl-L-alanyl-L-prolylmethyl)-N-isopropylcarbamate This compound was prepared following the procedure in Example 10: Yield, 43%; mp 165°–166° C.; NMR (CDCl$_3$) & 1.16 (d, 6H, J=7 Hz), 1.38 (d, 6H, J-7 Hz), 1.9–2.3 (m, 4H), 2.5–2.8 (m, 4H), 3.75 (S, 3H), 3.6–4.0 (m, 2H), 4.21 (S, 2H), 4.0–5.0 (m, 6H), 6.46 (d, 1H, J=7 Hz), 7.08 (d, 1H, J=7 Hz); IR (nujol) 3350, 1735, 1690, 1655, 1640, 1525 cm$^{-1}$. Anal. calcd. for C$_{25}$H$_{35}$N$_4$F$_7$O$_8$: C, 46.01; H, 5.41; N, 8.59. Found: C, 45.89; H, 5.42; N, 8.54.

EXAMPLE 61

S-Benzyl N-(N'-t-Boc-L-prolyl)methyl-N-isopropylthiocarbamate

This compound was prepared according to the procedure described in Example 6 starting with S-benzyl chlorothioformate (J. J. Willard and E. Pacsu, *J. Am. Chem. Soc.*, 82, 4317 (1960): NMR (CDCl$_3$) & 1.18 (d, 6H, J=7 Hz), 1.50 (S, 9H), 1.8–2.4 (m, 4H), 3.4–3.8 (m, 2H, 4.26 (S, 2H, 4.2–4.6 (m, 4H), 7.45 (S, 5H); IF (Film) 1740, 1690, 1640 cm$^{-1}$.

EXAMPLE 62

S-Benzyl N-(L-prolylmethyl)-N-isopropylthiocarbamate hydrochloride

This compound was prepared according to the procedure described in Example 8: mp 193°–194° C.; NMR (DMSO-d$_6$) & 1.10 (d, 6H, J=7 Hz), 1.6–2.3 (m, 4H), 3.0–3.5 (m, 2H), 4.6 (S, 2H), 4.46 (S, 2H), 4.2–4.8 (m, 2H), 7.41 (S, 5H), 9.7 (br, 2H), IR (Nujol) 1745, 1635, 1545 cm$^{-1}$.

EXAMPLE 63

S-Benzyl N-(Methyl succinyl-L-alanyl-L-alanyl-L-prolylmethyl)-N-isopropylthiocarbamate This compound was prepared according to the procedure described in Example 10: yield, 41%; mp 125°–127° C.; NMR (CDCl$_3$) & 1.0–1.5 (m, 12H), 1.7–2.3 (m, 4H), 2.4–2.8 (m, 4H), 3.4–3.9 (m, 2H), 3.80 (S, 3H) <4.0–4.9 (m, 9H), 7.50 (S, 5H): IR (Nujol) 3360, 1735, 1680, 1655, 1640, 1530 cm$^{-1}$. Anal. calcd. for C$^{28}$H$^{40}$N$^4$O$^7$S: (C, 58.23; H, 6.99, N, 9.71, S, 5.56 Found: C, 58.23, H, 7.00, N, 9.69, S, 5.55.

EXAMPLE 64

N-(N'-t-Boc-L-prolyl)methyl-N-methylamine

Sodium iodide (635 mg, 4.23 mmol) and 40% methylaine aqueous solution (6.9 ml, 80.6 mmol) were added to an ice-cooled solution of product from Example 4 (1.0 g, 4.03 mmol) in ethanol (10 ml). The mixture was shaken in a steel bomb at 65° C. for 12 h and the solvent evaporated. Saturated solutions of NaHCO$_3$ (5 ml) and NaCl (5 ml) were added to the residual mixture. The resulting mixture was extracted into ether, evaporated and purified by silica gel column chromatography (CHCl$^3$: CH$^3$OH, 50:1) to give 0.29 g (29.7%) of the title compound. NMR (CDCl$^3$) & 1.40 (s, 9H), 1.7–2.1 (m, 4H), 2.40 (s, 3H), 3.3–3.7 (m, 4H), 4.1–4.5 (m, 1H), IR (Film) 3340 (br), 1695 (br) c$^{-1}$.

EXAMPLE 65 p-Nitrophenyl
N-(N-t-Boc-L-prolylmethyl)-N-methylcarbamate

This compound was prepared in a manner similar to that for Example 6: yield 52%, NMR (CDCl$^3$) & 1.49 (s, 9H), 1.8–2.2 (m, 4H), 3.09–3.21 (br. s, 3H), 3.4–3.8 (m, 2H), 4.3–4.6 (m, 3H), 7.2–7.0 (m, 2H), 8.2–8.5 (m, 2H), IR (Film) 1740–1670, 1615, 1590, 1520, 1497 cm$^{-1}$.

EXAMPLE 66 p-Nitrophenyl N-(L-prolylmethyl)-N-methylcarbamate
hydrochloride

This compound was prepared using the procedure of Example 8: yield 74%; mp 177°–181° (dec); NMR (DMSO-d$^6$) & 1.7–2.3 (m, 4H), 2.9–3.7 (m, 5H), 4.4–4.8 (m, 3H), 7.3–7.7 (m, 2H), 8.2–8.5 (m, 2H); IR (Nujol) 3530, 3450, 1735, 1720, 1612, 1592, 1550, 1515 cm$^{-1}$.

EXAMPLE 67 p-Nitropheny N-(methyl
succinyl-L-alanyl-L-alanyl-L-prolymethyl)-N-methyl-
carbamate This compound was prepared using the procedure of Example 10: yield, 41%, mp 105°–110° C., NMR (CDCl$_3$) & 1.1–1.5 (m, 6H), 1.8–2.2 (m, 4H), 2.4–2.8 (m, 4H), 3.0–3.4 (m, 3H), 3.5–4.0 (m, 2H, 3.73 (S, 3H), 4.2–5.0 (m, 5H), 6.1–6.5 (m, 1H), 7.2–7.7 (m, 3H), 8.1–8.6 (m, 2H); IR (CHCl$_3$) 3300, 1735, 1640, 1520 cm$^{-1}$. Anal. Calcd. for C$_{25}$H$_{33}$N$_5$O$_{10}$: C, 53.28; H, 5.90; N, 12.43 Found: C, 53.53; H, 5.96; N, 12.36.

EXAMPLE 68

N-(N'-t-Boc-L-prolyl)methyl-N-t-butylamine

This compound was prepared following the same procedure as in Example 5: yield, 51%, NMR (CDCl$_3$) & 1.12 (S, 9H), 1.47 (S, 9H), 1.8–2.2 (m, 4H), 3.5–3.8 (m, 2H), 3.74 (S, 2H), 4.4–4.6 (m, 1H), IR (Film) 3320, 1710, 1690 cm$^{-1}$.

EXAMPLE 69 p-Nitrophenyl N-(N'-t-Boc-L-prolyl
methyl)-N-t-butylcarbamate

This compound was prepared using the procedure of Example 6: yellow oil, yield, 49%, NMR (CDCl$_3$) & 1.48 (S, 9H), 1.51 (s, 9H), 1.7–2.2 (m, 4H), 3.4–3.7 (m, 2H), 4.4–4.7 (m, 3H), 7.2–7.4 (m, 2H), 8.1–8.4 (m, 2H); IR (Film) 1740, 1690 (br), 1615, 1593 c$^{-1}$.

EXAMPLE 70 p-Nitrophenyl N-(L-prolymethyl)-N-t-butylcarbamate
hydrochloride

This compound was prepared using the procedure of Example 8: brown powder; yield, 61%; mp 85°–90° C. (dec); NMR (DMSO-d$_6$) & 1.41 (S, 9H), 1.7–2.2 (m, 4H), 2.8–3.5 (m, 2H), 4.0–4.9 (m, 3H), 6.9–7.5 (m, 2H), 8.0–8.4 (m, 2H).

EXAMPLE 71 p-Nitrophenyl N-(Methyl
succinyl-L-alanyl-L-alanyl-L-prolylmethyl-N-t-butyl-
carbamate This compound was prepared using the procedure of Example 10: colorless crystals; yield, 16%; mp 147°–151° C.; NMR (CDCl$_3$) & 1.1–1.8 (m, 15H), 1.8–2.3 (m 4H), 2.5–3.0 (m, 4H), 3.6–4.1 (m, 5H), 4.4–5.0 9 m, 5H), 6.2–6.7 (m, 1H), 6.9–7.7 (m, 3H), 8.0–8.6 (m, 2H); IR (CHCl$_3$) 3300, 1735, 1640, 1590, 1520 cm$^{-1}$. Anal. calcd. for C$_{28}$H$_{39}$N$_5$O$_{10}$: C, 55.53; H, 6.49; N, 11.56. Found: C, 55.42; H, 6.54; N, 11.51.

EXAMPLE 72

N-(N'-t-Boc-L-prolyl)methyl-N-isopropyl-2-thioxo-3-
thiazolidinecarboxamide

To a solution of N-(N'-t-Boc-L-prolyl)methyl-N-isopropylamine (1.7 g, 6.3 mmol) and Et$_3$N (1.09 ml, 7.8 mmol) in THF (20 ml) at 5° C. was added dropwise a solution of Compound (88) (1.12 g, 6.2 mmol) in THF (20 ml) for 3 min. The solution was stirred at 5° C. for 45 min and at r.t. for 2 hr. The precipitate was filtered off and the filtrate was evaporated in vacuo to give an oil. The oil was purified by column chromatography (silica gel 30 g) using 4% ethyl acetate in CH$_2$Cl$_2$ as an eluting solvent to give 1.3 g of product as an oil 50.5% yield. IR(CHCl$_3$): 0.9–1.5 (6H, m), 1.46 (9H, S), 1.8–2.2 (4H, m), 3.1–3.9 (4H, m), 3.9–5.0 (6H, m).

EXAMPLE 73

N-(L-Prolylmethyl)-N-isopropyl-2-thioxo-3-
thiazolidinecarboxamie Hydrochloride

HCl gas was passed through a solution of the compound of Example 72 (1.10 g, 2.60 mmol) in ethyl acetate (30 ml) at r.t. for 5 min. The solution was allowed to stand at r.t. for 20 min. The solution was evaporated in vacuo to give an oil residue which was triturated with ether to give a hydroscopic powder (0.70 g) of product 88.3% yield, IR (CDCl$_3$): 3400, 1735, 1690, 1435 cm$^{-1}$. NRM (&, DMSO-d$_6$): 0.9–1.3 (6H, m), 1.8–21. (4H, m), 3.0–4.7 (12H, m).

EXAMPLE 74

N-(Methyl
succinyl-L-alanyl-L-alanyl-L-prolylmethyl)-N-isopro-
pyl-2-thioxo-3-thiazolidinecarboxamide To a solution of methyl succinyl-L-alanyl-L-alanine (0.38 g, 1.38 mmol) and N-methylmorpholine (0.18 ml, 1.38 mmol) in acetonitrile (12 ml) at −15° C. was added a solution of isobutyl chloroformate (0.23 ml, 1.38 mmol) in acetonitrile (5 ml). The mixture was stirred at −15° C. for 10 min. To the mixture at −15° C. was added a suspension of the compound of Example 73 (0.5 g, 1.43 mmol) and N-methylmorpholine (0.18 ml, 1.64 mmol) in acetonitrile (14 ml). The mixture was stirred at −15° C. for 45 min and then at r.t. for 2 hr. The precipitate was filtered off and the filtrate was diluted with 10% aqueous citric acid and CH$_2$Cl$_2$. The organic layer was separated, dried over anhydrous MgSO$_4$, and evaporated in vacuo to give an oil. The oil was purified by column chromatography (silica gel 30 g) using 2% ethyl acetate in CH$_2$Cl$_2$ as an eluting solvent. The oil obtained was triturated with ether to give a powder of the compound (0.35 g)., 44.3% yield. mp. IR (CHCl$_3$): 3300, 1730, 1680, 1640, 1520, 1435 cm$^{-1}$. NMR (&, CDCl$_3$): 0.9–1.6 (12H, m), 2.10 (4H, m), 2.63 (4H, m), 30–5.0 (12H, m), 3.73 (3H, S), 6.60 (1H, br d, J=7 Hz), 7.16 (1H, m).

EXAMPLE 75

2-Pyridyl N-(N'-t-Boc-L-prolyl)methyl-N-isopropyl thiocarbamate

To a solution of N-(N'-t-Boc-L-prolyl)methyl-N-isopropylamine (2.0 g, 7.4 mmol) and Et$_3$N (1.2 ml, 8.6 mmol) in THF (12 ml) at 5° C. was added a solution of the compound of Example 89 (1.50 g, 8.64 mmol) IN THF (30 ml) for 3 min. The solution was stirred at 5° C. for 45 min and then at r.t. for 2 hr. The precipitate was filtered off and the filtrate was evaporated in vacuo to give an oil. The oil was purified by silica gel column chromatography (solvent, 5% ethyl acetate in CH$_2$Cl$_2$) to give 1.2 g of product as an oil 39.7% yield. IR (Film): 1735 (sh), 1690, 1615, 1570, 1560 cm$^{-1}$, NMR (&, CDCl$_3$); 1.23 (6H, d, J=6 Hz), 1.53 (9H, S), 1.9–2.3 (4H, m), 3.3–3.8 (2H, m), 4.1–5.0 (4H, m), 7.33 (1H, m), 7.80 (2H, m), 8.70 (1H, d, J=5 Hz).

EXAMPLE 76

2-pyridyl N-(L-prolylmethyl)-N-isopropylthiocarbamate Hydrochloride

HCl gas was passed through a solution of the compound of Example 75 (1.1 g, 2.7 mmol) in ethyl acetate (40 ml) at r.t. for 5 min. The solution was allowed to stand at r.t. for 20 min. Evaporation of the solvent gave a residue which was triturated with either to give a hygroscopic powder of product (0.7 g) 76.3% yield. IR (CHCl$_3$): 1740, 1645, 1605, 1545 cm$^{-1}$, NMR (&, DMSO-d$_6$): 1.1–1.6 (6H, m), 1.8–2.2 (4H, m), 3.1–3.5 (2H, m), 4.0–5.0 (4H, m), 7.5–8.2 (3H, m), 8.7 (1H, m).

EXAMPLE 77

2-Pyridyl N-(Methyl succinyl-L-alanyl-L-alanyl-L-prolylmethyl)-N-isopropylthiocarbamate To a solution of methyl succinyl-L-alanyl-L-alanine (0140 g, 1.46 mmol) and N-methylmorpholine (0.16 ml, 1.46 mmol) in THF (12 ml) at −15° C. was added a solution of isobutyl chloroformate (0.20 ml, 1.53 mmol) in THF (15 mol) for 3 min. The mixture was stirred at −15° C. for 10 min. To the mixture at −15° C. was added a suspension of the compound of Example 76. (0.50 g, 1.46 mmol) and N-methylmorpholine (0.19 ml, 1.73 mmol) in acetonitrile (14 ml). The mixture was stirred at −15° C. for 0.5 hr and then at r.t. for 2.5 hr. The reaction mixture was diluted with CH$_2$Cl$_2$. The organic layer was wahed with 10% aqueous citric acid, dried over anhydrous MgSO$_4$, and evaporated in vacuo to give an oil. The oil was triturated with ether to give a hygroscopic powder of desired compounds. (0.16 g). mp. 19.5% yield. IR (CHCl$_3$): 3300, 1730, 1650, 1520 cm$^{-1}$. NMR (&, CDCl$_3$): 1.1–1.6 (12H, m), 2.03 (4H, m), 2.60 (4H, m), 3.5–40 (2H, m), 3.66 (3H, S), 4.1–5.2 (6H, m), 6.76 (1H, d, J=8 Hz), 7.15–7.53 (2H, m), 7.66 (2H, m), 8.60 (1H, brd, J=5 Hz).

EXAMPLE 78

2-Benzothiazolyl N-(N'-t-Boc-L-prolyl)methyl-N-isopropylthiolcarbamate

To a solution of the compound of Example 5 (0.54 g, 2.0 mmol) and Et$_3$N (0.56 ml, 4.0 mmol) in THF (5 ml) at 5° C. was added a solution of compound 90 (0.9 g, 3.8 mmol) in THF (5 ml). The mixture was stirred at 5° C. for 2 hr. The reaction mixture was diluted with CH$_2$Cl$_2$. The organic layer was washed successively with H$_2$O, 10% aqueous citric acid, H$_2$O, and saturated NaCl solution, dried over anhydrous MgSO$_4$, and evaporated in vacuo to give an oil. The oil was purified by silica gel column chromatography (solvent, CHCl$_3$) to give a 0.51 g of the compound as an oil. 55.1% yield. IR (Film): 1735, 1680, 1390, 1150 cm$^{-1}$. NMR (&, CDCl$_3$): 1.27 (6H, d, J=7 Hz), 1.50 (9H, S), 1.8–2.2 (4H, m), 3.50 (2H, m), 4.0–4.7 (4H, m), 7.20–7.66 (2H, m), 7.80–8.20 (2H, m).

EXAMPLE 79

2-Benzothizolyl N-(L-prolylmethyl)-N-isopropylthiocarbamate

HCl gas was passed through a solution of the compound of Example 78 (0.51 g, 1.1 mmol) in a mixture of ethyl acetate (7 ml) and formic acid (1 ml) at 5° C. for 5 min. The solution was allowed to stand at r.t. for 10 min and then evaporated in vacuo. To the oily residue was added ethyl acetate and the ethyl acetate was evaporated in vacuo. This operation was repeated three times. The residue obtained was triturated with ether to give a powder which was collected and washed with ether to give the compound (0.36 g), 82.3% yield. mp. 150°–156° C. IR (Nujol): 1745, 1655, 1545 cm$^-$. NMR (&, DMSO-d$_6$): 1.23 (6H, d, 7 Hz), 1.7–2.2 (4H, m), 3.0–3.6 (2H, m), 4.0–5.0 (4H, m), 7.43–7.66 (2H, m), 7.9–8.3 (2H, m). Anal. calcd. for C$_{17}$H$_{21}$N$_3$O$_2$S$_2$.HCl.0.5H$_2$O: C, 49.93; H, 5.67; N, 10.27. Found: c, 49.94, H, 5.64; N, 10.40.

EXAMPLE 80

2-Benzothiazolyl N-(methyl succinyl-L-alanyl-L-alanyl-L-prolylmethyl)-N-isopropylthiocarbamate To a solution of methyl succinyl-L-alanyl-L-alanine (0.257 g, 0.936 mmol) and N-methylmorpholine (94.5 mg, 0.936 mmol) in acetonitrile (4 ml) at −15° C. was added a solution of isobutyl chloroformate (128 mg, 0.936 mmol) in acetonitrile (2 ml). The mixture was stirred at −15° C. and there was added a suspension of the compound of Example 79 (0.340 g, 0.851 mmol) and N-methylmorpholine (103 mg, 1.02 mmol) in acetonitrile (6 ml). The mixture was stirred at −10° C. for 15 min and then at 5° C. for 1 hr 50 min. The reaction mixture was diluted with CH$_2$Cl$_2$. The organic layer was washed successively with 10% aqueous citric acid, water, and saturated NaCl solution and dried over anhydrous MgSO$_4$. Evaporation of the solvent gave a crude oil which was purified by silica gel column chromatography (solvent, 3% methanol in CH$_2$Cl$_2$) to give a 0.47 g of crystalline residue. Recrystallization of the crystals from tethyl acetate-hexane gave 0.35 g of desired compound. 66.4% yield. mp 169°–171° C. IR (Nujol): 3350, 1730, 1690, 1655, 1530 cm$^{-1}$. NMR (&, CDCl$_3$): 1.0–1.6 (12H, m), 2.1 (4H, m), 2.63 (4H, m), 3.5–4.0 (2H, m), 3,70 (3H, S), 4.0–5.1 (6H, m), 7.03 (1H, brd, J=7 Hz), 7.3–8.2, (5H, m). Anal. Calcd. for C$_{28}$H$_{37}$N$_5$O$_7$S$_2$: C, 54.27; H, 6.02; N, 11.30. Found=C, 54.15; H, 6.03; N, 11.22.

EXAMPLE 81

1-Propyl-5-tetrazolyl N-(N'-5-Boc-L-prolyl)methyl-N-isopropylthiocarbamate

To a solution of a compound 5 (2.38 g, 8.8 mmol) and Et$_3$N (1.76 g, 0.0174 mol) in acetonitrile (10 ml) at 5° C.

was added a solution of the compound of Example 91. (3.0 g, 0.015 mol) in acetonitrile (8 ml) for 3 min. The mixture was stirred at 5° C. for 1 hr and then at r.t. for 2 hrs. The reaction mixture was evaorated in vacuo to give a residue which was dissolved in $CH_2Cl_2$. The $CH_2Cl_2$ layer was washed with $H_2O$ and saturated NaCl solution, dried over anhydrous $MgSO_4$, and evaporated in vacuo. The oil was purified by silica gel column chromatography (solvent, 10% ethyl acetate in $CH_2Cl_2$) to give 1.1 g of the compound as an oil. 29.8% yield. IR (Film): 1735, 1680, 1390 cm$^{-1}$. NMR (&, $CDCl_3$): 1.00 (3H, t, J=7 Hz), 1.33 (6H, d, J=7 Hz), 1.50 (9H, S), 1.8–2.4 (6H, m), 3.53 (2H, m), 4.0–4.8 (4H, m), 4.37 (2H, t, J=7 Hz.

EXAMPLE 82

1-Propyl-5-tetrazolyl N-(L-prolylmethyl)-N-isopropylthiocarbamate Hydrochloride

HCl gas was passed through a solution of the compound of Example 81 (1.1 g, 2.6 mmol) in a mixture of ethyl acetate (8 ml) and formic acid (6 ml) ar r.t. for 3 min. The solution was allowed to stand at r.t. for 10 min. The reaction mixture was evaporated in vacuo to give an oil. To this oil was added ethyl acetate and the ethyl acetate was evaporated in vacuo. The oil was triturated with ether to give a hygroscopic powder of 90 (0.4 g). NMR (&, DMSO-d$_6$)=0.9–1.6 (9H, m), 1.7–2.3 (6H, m), 3.2–4.0 (2H, m), 4.0–5.0 (6H, m).

EXAMPLE 83

1-Propyl-5-tetrazolyl N-(methyl succinyl-L-analyl-L-alanyl-L-prolylmethyl)-N-isopropylthiocarbamate To a solution of methyl succinyl-L-Alanyl-L-alanine (0.325 g, 1.31 mmol) and N-methylmorpholine (0.132 g, 1.31 mmol) in THF (3 ml) at −15° C. was added a solution of isobutyl chloroformate (0.179 g, 1.31 mmol) in THF (1 ml). The mixture was stirred at −15° C. for 10 min. To the mixture was added a suspension of the compound of Example 83 (0.35 g, 0.93 mmol) and N-methylmorpholine (0.15 g, 1.5 mmol) in acetonitrile (4 ml). The mixture was stirred at −10° C. for 0.5 hr and then at 5° C. for 4 hrs. The reaction mixture was diluted with $CH_2Cl$. The organic layer was washed successively with 10% aqueous citric acid, water and saturated NaCl solution, dried over $MgSO_4$, and evaporated in vacuo. The oil obtained was purified by silica gel column chromatography (solvent, 3% methanol in $CHCl_3$) to give 0.13 g of the compound as an oil. The oil was crystallized from ethyl acetate-hexane to give 39 mg. 7.0% yield, mp 107°–108° C. IR (Nujol): 3350, 1735, 1685, 1655, 1530 cm$^{-1}$. NMR (& $CDCl_3$): 1.00 (3H, t, J=7 Hz), 1.0–1.7 (12H, m), 1.7–2.3 (6h, m), 2.66 (4H, m), 3.5–4.0 (2H, m), 3.70 (3H S), 4.0–5.1 (8H, m), 6.83 (1H, d, 8 Hz), 7.50 (1H, m).

EXAMPLE 84

N-N'-t-Boc-L-prolyl)methyl-N-2-propynylamine

To a solution of (N-t-Boc-L-prolyl)chloromethane (2.0 g, 8.1 mmol) in ether (50 ml) at 5° C. was added 2-propynylamine (2.2 ml, 0.032 mol). The solution was stirred at 5° C. for 1.5 hr and then at r.t. for 1 hr. The precipitate was filtered off and washed with ether. The filtrate was evaporated in vacuo to give an oil. The oil was purified by silica gel column chromatography (solvent, 3% methanol in $CHCl_3$) to give 1.1 g of the compound as an oil. 51% yield, IR (Film): 3200–3500, 1690, 1400 cm$^{-1}$. NMR (&, $CDCl_3$): 1.43 (9H, S), 1.7–2.1 (4H, m), 2.30 (1H, brS), 3.3–3.8 (6H, m), 4.3 (1H, m).

EXAMPLE 85 p-Nitrophenyl N-(N'-5-Boc-L-prolyl)methyl-N-2-propynylcarbamate

To a solution of the compound of Example 84 (1.0 g, 3.76 mmol) and Et$_3$N (0.65 ml, 4.7 mmol) in THF (12 ml) at 5° C. was added a solution of p-nitrophenyl chloroformate (0.75 g, 3.72 mmol) in THF (4 ml). The mixture was stirred at 5° C. for 1 hr and then at r.t. for 2 hr. The reaction mixture was filtered and the filtrate was evaporated in vacuo. The oil was purified by silica gel column chromatography (solvent, $CHCl_3$) to give an oil (1.60 g). 98.9% yield, IR (Film): 1730, 1680, 1610, 1590 cm$^{-1}$. NMR (&, $CDCl_3$): 1.43 (9H, S), 2.0 (4H, m), 2.43 (1H, brS), 3.6–4.8 (7H, m), 7.43 (2H, m), 8.33 (2H, brd, J=8 Hz).

EXAMPLE 86

P-Nitrophenyl N-(L-prolylmethyl)-N-2-propynylcarbamate Hydrochloride

HCl gas was passed through a solution of the compound of Example 85. (1.40 g, 3.25 mmol) in ether (40 ml) at r.t. for 5 min. The solution was allowed to stand at r.t. for 15 min. The reaction mixture was evaporated in vacuo to give a residue. Trituration of the oil with ether gave a powder (0.36 g) of the compound. 30.1% yield, mp 141°–152° C. IR (Nujol): 3300, 1740, 1720, 1610, 1590, 1515 cm$^{-1}$. NMR (&, DMSO-d$_6$): 2.0 (4H, m), 2.40 (1H, brS), 3.3–3.7 (2H, m), 4.0–4.8 (5H, m), 7.40 (2H, brd, J=8 Hz), 8.30 (2H, d, J=8 Hz).

EXAMPLE 87

-p-Nitrophenyl N-(methyl succinyl-L-alanyl-L-alanyl-L-prolylmethyl)-N-propynylcarbamate To a solution of methyl succinyl-L-alanyl-L-alanine (0.27 g, 0.99 mmol) and N-methylmorpholine (0.11 ml, 1.0 mmol) in THF (12 ml) at −15° C. was added a solution of isobutyl chloroformate (0.13 g, 0.95 mmol) in THF. The mixture was stirred at −15° C. for 15 min. To the mixture was added a mixture of the compound 86 (0.35 g, 0.95 mmol), N-methylmorpholine (0.11 ml, 1.0 mmol), and bis(trimethylsilyl)acetamide (1.5 ml) in THF (14 ml). The mixture was stirred at −15° C. for 1 hr. and then at r.t. for 2.5 hr. The reaction mixture was diluted with $CH_2Cl_2$. The organic layer was washed with 10% aqueous citric acid, dried over anhydrous $MgSO_4$, and evaporated in vacuo to give an oil. The oil was purified by silica gel column chromatography (solvent, 5% methanol in $CHCl_3$) to give an oil. Trituration with ether gave a powder (0.21 g) of the compound. 37.7% yield. mp. 160°–163° C. IR (Nujol): 3340, 1740, 1690, 1655, 1635, 1595, 1520 cm$^{-1}$. NMR (&, $CDCl_3$): 1.33 (6H, d, J=7 Hz), 2.03 (4H, m), 2.40 (1H, brS), 2.60 (4H, m), 3.5–4.0 (2.H, m), 3.70 (3H, S), 4.1–5.0 (7H, m), 6.40 (1H, m), 7.10 (1H, d, J=7 Hz), 7.33 (2H, m), 8.30 (2H, d, J=9 Hz).

EXAMPLE 88

2-Thioxo 3-thiazolidinecarbonyl chloride

A solution of 2-mercaptothiazoline (2.0 g, 0.0168 mmol) and Et$_3$N (2.9 ml, 0.021 mol) in THF (30 ml) was added dropwise to a solution of phosgene (2.37 g, 0.0239 mol) in toluene (12 ml) at 5° C. for 7 min. The mixture was stirred at 5° C. for 5 min and then filtered to remove the precipitate. The filtrate was evaporated in vacuo to give a crystalline residue. To the residue was added ether (10 ml) and the ether was evaporated in vacuo. This operation was repeated twice. 2-Thioxo-3-thiazolidinecarbonyl chloride (2,0 g) was obtained as a solid. 65.5% yield. IR (Nujol).

EXAMPLE 89

2-Pyridyl thiochloroformate

A solution of 2-mercaptopyridine (1.50 g, 0.0135 mol) and Et$_3$N (2.5 ml, 0.018 mol) in THF (24 ml) was added dropwise to a solution of phosgene (1.53 g, 0.015 mol) in toluene (8 ml) at 5° C. for 6 min. The mixture was stirred at 5° C. for 5 min and then at r.t. for 5 min. The reaction mixture was filtered and the filtrate was evaporated in vacuo. To the residue was added ether and the ether was evaporated. This operation was repeated twice. An oil of the compound (1.5 g) was obtained. 63.9% yield. IR (Film): 1765 c$^{-1}$.

EXAMPLE 90

2-Benzothiazolyl thiochloroformate

A solution of 2-mercaptobenzothiazole (0.669 g, 4.0 mmol) and Et$_3$N (0.61 ml, 4.4 mmol) in THF (5 ml) was added to a solution of phosgene (0.59 g, 6.0 mmol) in toluene (3.1 ml) at 5° C. for 15 min. To the mixture was added acetonitrile (3 ml). The mixture was stirred at 5° C. for 0.5 hr. The precipitate was filtered and washed with THF. The filtrate was evaporated in vacuo to give a solid (0.9 g). IR (Nujol)=1775, 1605 cm$^{-1}$.

EXAMPLE 91

1-Propyl-5-tetrazolyl thiochloroformate

A solution of 5-mercapto-1-propyltetrazole (2.5 g, 0.0174 mol) and Et$_3$N (2.65 ml, 0.0101 mol) in acetonitrile (10 ml) was added to the solution of phosgene (2.58 g, 0.0260 mol) in toluene (13.5 ml) at 5° C. for 50 min. The mixture was stirred at 5° C. for 50 min. The precipitate was filtered off and washed with THF. The filtrate was evaporated in vacuo to give an oil (3.1 g). IR (Film): 1775, 1720 cm$^{-1}$. NMR (&, CDCl$_3$)=1.00 (3H, t, J=7 Hz), 2.10 (2H, m), 4.50 (2H, m).

EXAMPLE 92

N-Trifluoroacetyl-L-alanyl-L-alanine

This compound was prepared according to the method by Schallenberg et al [E. E. Schallenberg and M. Calvin, *J. Amer. Chem. Soc.* 77, 2779 (1955); J. L. Dimicoli et al. *Biochemistry* 15, 2230 (1976)]; yield based on alanyl-a-alanine, 71.3%; mp 225°–235° C. (dec) NMR (DMSO-d$_6$ & 1.42 (d, J=7 Hz, 3H), 1.46 (d, J=7 Hz, 3H), 4.54 (l, J=7 Hz, 2H), 7.92 (d, J=8 Hz, 1H), 8.46 (d, J=7 Hz, 1H); IR (Nujol) 3330, 3310, 3270, 1705, 1665, 1545 cm$^{-1}$.

EXAMPLE 93

Pentafluorophenyl N-(trifluoroacetyl-L-alanyl-L-alanyl-L-prolylmethyl)-N-isopropylcarbamate This compound was prepared in a similar manner as Example 10 colorless powder; yield 20.3%, mp 85°–88° C., NMR (CDCl$_3$), & 0.9–1.9 (m, 12H), 1.9–2.5 (m, 4H), 3.3–5.0 (m, 8H), IR (Film) 3420 (b), 1715, 1670, 1555 cm$^{-1}$. Anal. calcd for C$_{24}$H$_{26}$N$_4$F$_8$O$_6$: C, 46.61; H, 4.24; N, 9.06. Found C, 46.74, H, 4.27, N, 9.04.

EXAMPLE 94

Heptafluorobutyl chloroformate

Triethylamine (3.66 ml, 26.3 mmol) was added dropwise to a solution of heptafluorobutanol (3.1 ml, 25 mmol) and phosgene (3.3 g, 30 mmol) in benzene (26 ml) at 5° C. The mixture was stirred at 5° C. for 30 min and at room temperature for 2 h, filtered and distilled. The product distilled with benzene and was was used in the next step without further purification. NMR (CDCl$_3$) & 4.70 (5, 2H, J=12.5 Hz; IR (Film) 1785 cm$^{-1}$.

EXAMPLE 95

Pentafluorophenyl chloroformate

This compound was prepared according to the procedure in Example 94: IR (Film) 1800, 1525 cm$^{-1}$.

EXAMPLE 86

1-Phenyl-5-tetrazolyl chlorodithioformate

To a solution of thiophosgene (1.29 g, 0.0112 mol) in THF (40 ml) at 5° C. was added a solution of 1-phenyl-1H-tetrazole-5-thiol (2.0 g, 0.0112 mol) and Et$_3$N (1.94 ml, 0.0134 mol) in THF (30 ml). The mixture was stirred at 5° C. for 30 min and then at r.t. for 1 hr. 20 min. The precipitate was filtered and washed with THF. The filtrate was evaporated in vacuo. To the obtained residue was added ether and the insoluble material was filtered off. The filtrate was evaporated in vacuo to give a solid which was recrystallized from CHCl$_3$—hexane. 0.91 g of the compound was obtained. 27.6% yield. IR (Nujol): 1725, 1585 cm$^{-1}$.

EXAMPLE 97

1-Phenyl-5-tetrazolyl N-(N'-5-Boc-L-prolyl)methyl-N-isopropyldithiocarbamate

To a solution of compound 5 (1.30 g, 4.81 mmol) and Et$_3$N (0.83 ml, 5.7 mmol) in THF (14 ml) at 5° C. was added a solution of the compound of Example 96 (1.40 g, 4.77 mmol in THF (14 ml) for 10 min. The solution was stirred at 5° C. for 2 hr and then at r.t. for 2 hr. The precipitate was filtered and washed with THF. The filtrate was evaporated in vacuo and the obtained oil was purified by silica gel column chromatography (solvent, CHCl$_3$) to give 1.30 g of the compound as an oil. 51.8% yield. IR (Film): 1740, 1690, 1595, 1395 cm$^{-1}$. NMR (&, CDCl$_3$): 1.0–1.6 (6H, m), 1.50 (9H, S), 1.8–2.3 (4H, m), 3.3–4.8 (6H, m), 7.63 (5H, S).

EXAMPLE 98

1-Phenyl-5-tetrazolyl N-(L-prolylmethyl)-N-isopropyldithiocarbamate Hydrochloride HCl gas was passed through a solution of compound 97 (1.20 g, 2.28 mmol) in ether (50 ml) at r.t. for 8 min. The solution was allowed to stand at r.t. for 15 min. The reaction mixture was evaporated in vacuo to give an oil of the compound (0.85 g), 87.4% yield. NMR (&, DMSO-d$_6$): 1.0–1.6 (6H, m), 1.8–2.3 (4H, m), 3.3–4.8 (6H, m), 7.73 (5H, S).

EXAMPLE 99

1-Phenyl-5-tetrazolyl N-(methyl succinyl-L-alanyl-L-alanyl-L-prolylmethyl)-N-isopropyldithiocarbamate To a solution of methyl succinyl-L-alanyl-L-alanine (9.60 g, 2.20 mmol) and N-methylmorpholine (9.24 ml, 2.19 mmol) in THF (20 ml) at −15° was added a solution of isobutyl chloroformate (0.28 ml, 2.13 mmol) in THF (5 ml). The mixture was stirred at −15° C. for 15 min. To the mixture was added a mixture of compound 98 (0.80 g, 1.86 mmol), N-methylmorpholine (0.24 ml, 2.19 mmol), and bis(trimethylsilyl)acetamide (2 ml) in THF (14 ml). The mixture was stirred at −15°C for 0.5 hr and then at r.t. for 2 hr. The reaction mixture was diluted with CHCl$_3$. The organic layer was washed with 10% aqueous citric acid, dried over anhydrous MgSO$_4$, and evaporated in vacuo to give an oil. The oil was crystallized from CHCl$_3$-hexane to give crystals of compound 99. NMR (&, CDCl$_3$); 0.9–1.6 (12H, m), 2.0 (4H, m), 2.53 (4H, m), 3.5–3.8 (2H, m), 3.63 (3H, s), 4.0–5.0 (6H, m), 7.0 (1H, m), 7.13–7.8 (5H, m).

The procedures described in Schemes I and II above and the following Schemes III, IV, V and VI were followed in preparing the compounds of the working examples described above. Set forth hereinafter are Schemes III, IV, V and VI with the compounds prepared in the examples being indicated. The compounds of the intermediates and final products are identified by example numbers adjacent the definitions of R and R′.

Scheme III

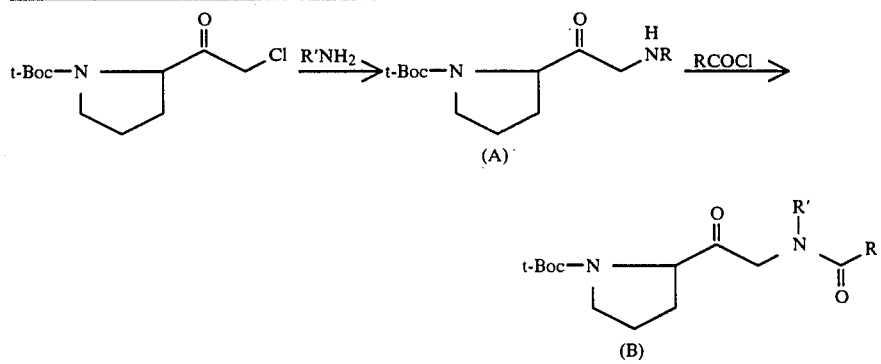

(A)

(B)

| A | B |
|---|---|
| 5: R′ = CH(CH$_3$)$_2$ | 15: R′ = CH(CH$_3$)$_2$, R = SMT |
| 18: R′ = 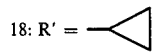 | 19: R′ = 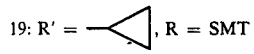, R = SMT |
| 22: R′ = —CH$_2$CH$_2$CH$_3$ | 23: R′ = n-C$_3$H$_7$, R = SMT |
| 32: R′ = n-C$_4$H$_9$ | 26: R′ = n-C$_3$H$_7$, R = ONP |
| 39: R′ = CH$_2$CH=CH$_2$ | 29: R′ = 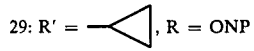, R = ONP |
| 43: R′ = CH$_2$CH(CH$_3$)$_2$ | 33: R′ = n-C$_4$H$_9$, R = SMT |
| 47: R′ = CH$_2$Ph | 36: R′ = CH(CH$_3$)$_2$, R = 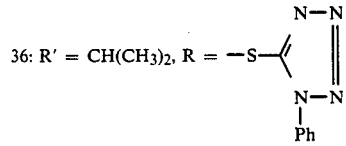 |
| 52: R′ = 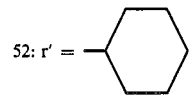 | 40: R′ = CH$_2$CH=CH$_2$, R = SMT |
| | 44: R′ = CH$_2$CH(CH$_3$)$_2$, R = ONP |
| | 48: R′ = CH$_2$Ph, R = ONP |
| | 52: R′ = 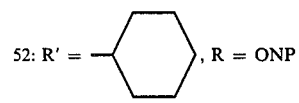, R = ONP |

Scheme III

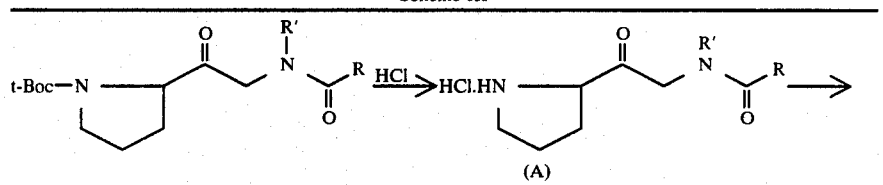

(A)

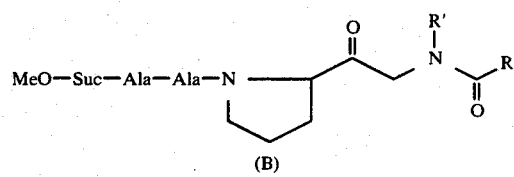

(B)

| A | B |
|---|---|
| 16: R' = i-C₃H₇, R = SMT | 17: R' = i-C₃H₇, R = SMT |
| 20: R' = ▷, R = SMT | 21: R' = ▷, R = SMT |
| 24: R' = n-C₃H₇, R = SMT | 25: R' = n-C₃H₇, R = SMT |
| 27: R' = n-C₃H₇, R = ONP | 28: R' = n-C₃H₇, R = ONP |
| 30: R' = ▷, R = ONP | 31: R' = ▷, R = ONP |
| 34: R' = n-C₄H₉, R = SMT | 35: R' = n-C₄H₉, R = SMT |
| 37: R' = i-C₃H₇, R = (tetrazole-SMT-C₆H₅) | 38: R' = i-C₃H₇, R = (tetrazole-SMT-C₆H₅) |
| 41: R' = CH₂CH=CH₂, R = SMT | 42: R' = CH₂CH=CH₂, R = SMT |
| 45: R' = CH₂CH(CH₃)₂, R = ONP | 46: R' = CH₂CH(CH₃)₂, R = ONP |
| 49: R' = CH₂Ph, R = ONP | 50: R' = CH₂Ph, R = ONP |
| 53: R' = cyclohexyl, R = ONP | 53: R' = cyclohexyl, R = ONP |

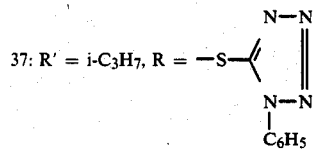 $\xrightarrow{\text{R'NH}_2}$ 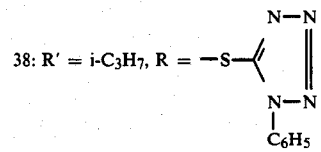 $\xrightarrow{\text{RCOCl}}$ (A)

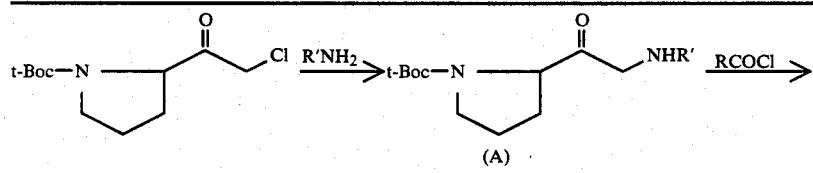

(B)

| A | B |
|---|---|
| 64: R' = CH₃ | 55: R' = CH(CH₃)₂, R = 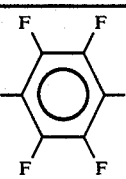 (pentafluorophenoxy) |
| 68: R' = C(CH₃)₃ | 58: R' = CH(CH₃)₂, R = OCH₂CF₂CF₂CF₃ |

-continued
Scheme III

84: R' = CH₂C≡CH

61: R' = CH(CH₃)₂, R = —S—CH₂—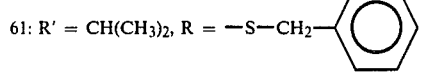

69: R' = C(CH₃)₃, R = ONP

72: R' = CH(CH₃)₂, R = 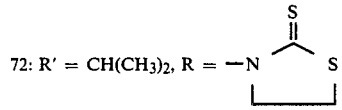

75: R' = CH(CH₃)₂, R = —S—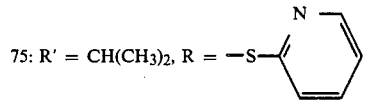

78: R' = CH(CH₃)₂, R = —S—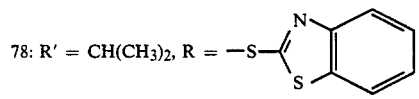

81: R' = CH(CH₃)₂, R = —S—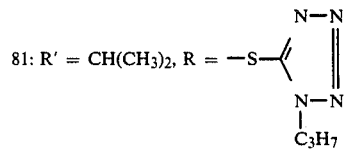

85: R' = CH₂C≡CH, R = ONP

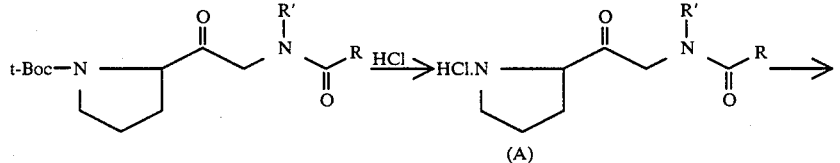
(A)

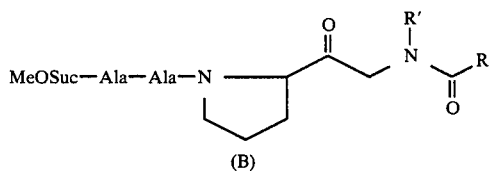
(B)

| A | B |
|---|---|
| 56: R' = CH(CH₃)₂, R = —O—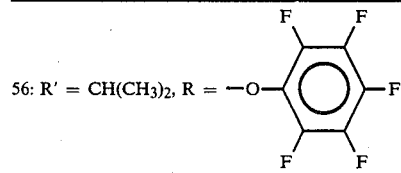 | 57: R' = CH(CH₃)₂, R = O—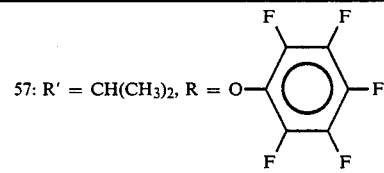 |
| 59: R' = CH(CH₃)₂, R = OCH₂CF₂CF₂CF₃ | 60: R' = CH(CH₃)₂, R = OCH₂CF₂CF₂CF₃ |
| 62: R' = CH(CH₃)₂, R = —SCH₂—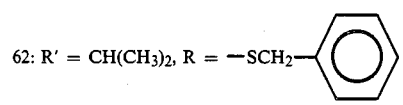 | 63: R' = CH(CH₃)₂, R = —SCH₂—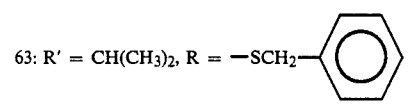 |
| 66: R' = CH₃, R = ONP<br>70: R' = C(CH₃)₃, R = ONP | 67: R' = CH₃, R = ONP<br>72: R' = C(CH₃)₃, R = ONP |
| 73: R' = CH(CH₃)₂, R = 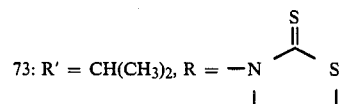 | 74: R' = CH(CH₃)₂, R = 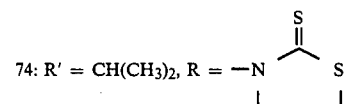 |

4,643,991
Scheme III -continued
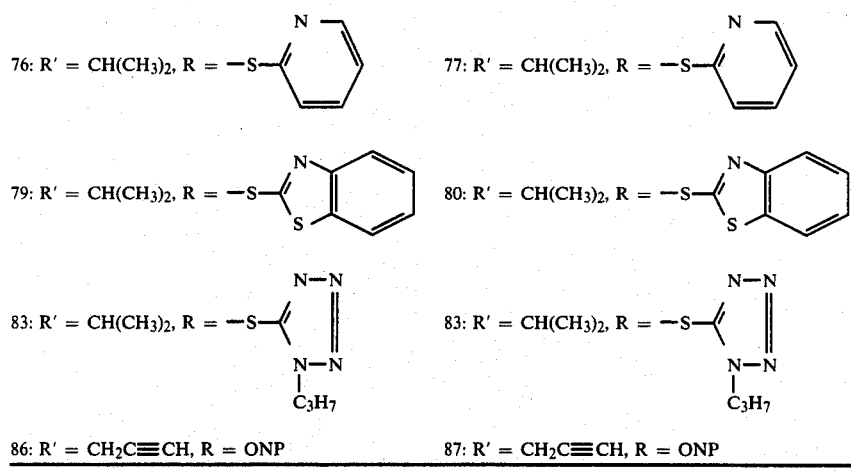
76: R' = CH(CH₃)₂, R = —S-pyridyl    77: R' = CH(CH₃)₂, R = —S-pyridyl
79: R' = CH(CH₃)₂, R = —S-benzothiazolyl    80: R' = CH(CH₃)₂, R = —S-benzothiazolyl
83: R' = CH(CH₃)₂, R = —S-tetrazolyl(C₃H₇)    83: R' = CH(CH₃)₂, R = —S-tetrazolyl(C₃H₇)
86: R' = CH₂C≡CH, R = ONP    87: R' = CH₂C≡CH, R = ONP
Scheme IV
R—H + COCl₂ ⟶ RCOCl.
(A)
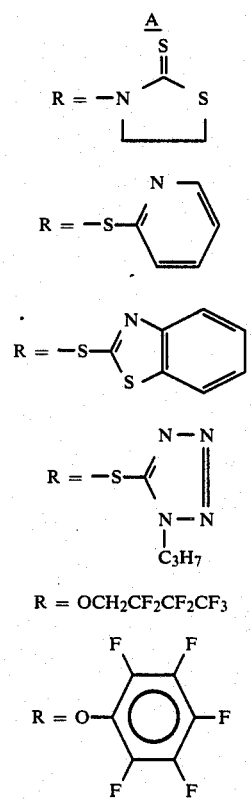
R = OCH₂CF₂CF₂CF₃
R = O-pentafluorophenyl
Scheme V
CF₃CO—Ala—Ala +
92
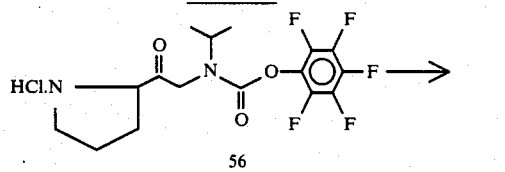
56
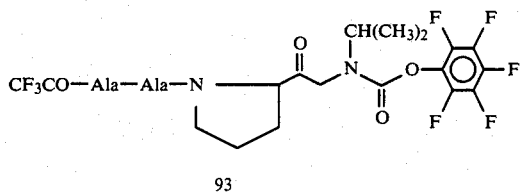
93
Scheme VI
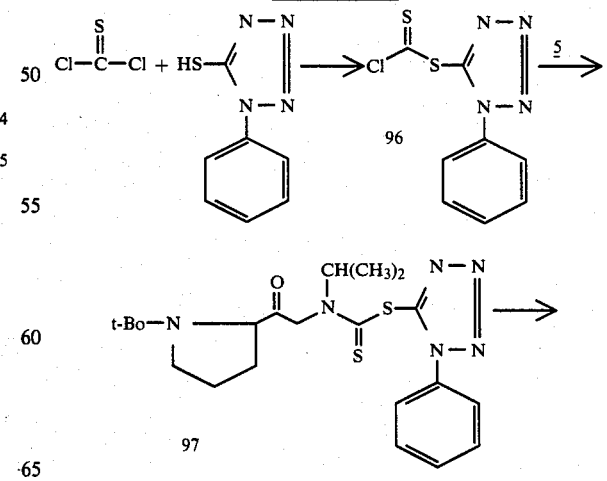

-continued
Scheme VI

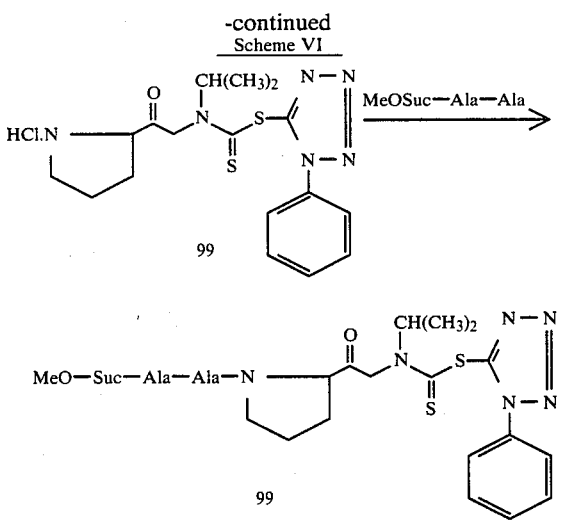

As pointed out above, the compounds of the invention are useful as elastase inhibitors. To evaluate the compounds, the inhibitory activity of the compounds were tested in vitro against the serine dependent proteolytic enzymes, trypsin, chymotrypsin and porcine pancreatic elastase. All three enzymes belong to the family of serine proteases where the catalytic residues are composed of a triad of amino acid residues, serine, histidine and aspartic acid that actually perform the peptide bond hydrolysis. In addition to the catalytic residues, the active site is composed of an extended substrate binding site that consists of a primary substrate binding site $S_1$, and various subsites on either side of the scissile bond.

The terminology of Schechter and Berger, Biochem. Biophys. Res. Commun., 27, 157 1980) is used where $S_2$-$S_1$-$S_1'$-$S_2'$ refer to subsites on both sides of the catalytic site of the enzyme and the notation P on the substrate (or inhibitor) denotes amino acid residues which bind to these enzyme subsites, such that $P_1$-$P_1'$ represents the bond which is cleaved. Substrate specificity studies with HL elastase, Powers et al, Biochem, Biophys, Acta., 485, p. 156, (1977), have shown that substrates with the sequence MeOSuc-Ala-Ala-Pro-Val (representing $P_5$-$P_4$-$P_3$-$P_2$-$P_1$ are highly reactive with the enzyme. The same sequence, although not ideal with PP elastase, was found to react with it effectively. In fact, HL elastase is similar to the more widely studied PP elastase in many respects. They are both serine proteases that show esterase activity toward synthetic substrates such as Boc-Ala-ONp and are both inhibited by $\alpha_1$-anti-trypsin. Furthermore, the natural substrates of these enzymes are very similar.

The results of these evaluations are set forth in the following Tables 1, 2, and 3. The compounds tested as shown in Tables 1, 2, 3, and 4 were prepared as described above.

TABLE 1

| Compound No. | Peptidyl Carbamates (ROCONR'R") where NR'R" is a Polypeptide Effect of changes in $P_1'$ on inhibitory activity towards PP elastase.(*) | Ki (μM) | Comments | mp$^a$ (°C.) |
|---|---|---|---|---|
| 10 | MeOSuc—Ala—Ala—Pro—CH$_2$—N—CO—O—⟨phenyl⟩—NO$_2$  (N-isopropyl)  $P_1'$ | 42.5 | + | 153–163 |
| 11 | MeOSuc—Ala—Ala—Pro—CH$_2$—N—CO—O—⟨phenyl⟩  (N-isopropyl) | 32.5 | + | 60–65 |
| 58 | MeOSuc—Ala—Ala—Pro—CH$_2$—N—CO—O—⟨C$_6$F$_5$⟩  (N-isopropyl) | 37.5 | + | 152–154 |
| 61 | MeOSuc—Ala—Ala—Pro—CH$_2$—N—CO—O CH$_2$CF$_2$CF$_2$CF$_3$  (N-isopropyl) |  | + | 165–166 |
| 64 | MeOSuc—Ala—Ala—Pro—CH$_2$—N—CO—SCH$_2$—⟨phenyl⟩  (N-isopropyl) |  | − | 125–127 |
| 18 | MeOSuc—Ala—Ala—Pro—CH$_2$—N—CO—S—⟨thiadiazole-N-CH$_3$⟩  (N-isopropyl) | 14.8 | + | 84–87 |

TABLE 1-continued

Peptidyl Carbamates (ROCONR'R") where NR'R" is a Polypeptide
Effect of changes in $P_1'$ on inhibitory activity towards PP elastase.(*)

| Compound No. | Ki (μM) | Comments | mp$^a$ (°C.) |
|---|---|---|---|
|  | — |  | ~50 |

(*)NONE OF THE LISTED COMPOUNDS EXHIBITED INHIBITION TOWARDS TRYPSIN AND CHYMOTRYPSIN

+ AT LEAST 70% INHIBITION OF PP ELASTASE OBSERVED IN 30 MIN AT $\frac{[I]}{[E]}$ = 260, [I] ~ 150 μM

− NO INHIBITION OF PP ELASTASE AT [I] < 150 μM USING [E] = 0.61 μM $^a$ALL COMPOUNDS WERE NOVEL AND WERE IDENTIFIED BY SPECTRAL DATA AND ELEMENTAL ANALYSES.

TABLE 2

Peptidyl Carbamates (ROCONR'R") where R'R"N is a Polypeptide:
Effect of changes in $P_1$ on inhibitory activity towards PP elastase.(*)

| Compound No. | Structure | Ki (μM) | Comments | mp$^a$ (°C.) |
|---|---|---|---|---|
| 10 | MeOSuc—Ala—Ala—Pro—CH$_2$—N(iPr)—CO—O—C$_6$H$_4$—NO$_2$ | 42.5 | + | 153–163 |
| 29 | MeOSuc—Ala—Ala—Pro—CH$_2$—N(sBu)—CO—O—C$_6$H$_4$—NO$_2$ | 30.5 | + | 161–166 |
| 32 | MeOSuc—Ala—Ala—Pro—CH$_2$—N(cyclopropyl)—CO—O—C$_6$H$_4$—NO$_2$ |  | + | 155–160 |
| 68 | MeOSuc—Ala—Ala—Pro—CH$_2$—NH—CO—O—C$_6$H$_4$—NO$_2$ |  | + | 105–110 |
| 72 | MeOSuc—Ala—Ala—Pro—CH$_2$—NN(+)—CO—O—C$_6$H$_4$—NO$_2$ |  | — | 147–151 |

(*)NONE OF THE LISTED COMPOUNDS EXHIBITED INHIBITION TOWARDS TRYPSIN AND CHYMOTRYPSIN

+ AT LEAST 70% INHIBITION OF PP ELASTASE OBSERVED IN 30 MIN AT $\frac{[I]}{[E]}$ = 260, [I] ~ 150 μM

− NO INHIBITION OF PP ELASTASE AT [I] < 150 μM USING [E] = 0.61 μM $^a$ALL COMPOUNDS WERE NOVEL AND WERE IDENTIFIED BY SPECTRAL DATA AND ELEMENTAL ANALYSIS.

TABLE 3

Peptidyl Carbamates (ROCONR'R") where R'R"N is a polypeptide
Effect of Variations in $P_5$ and $P_3$ on inhibitory activity towards PP elastase

| Compound No. | Structure | Ki (μM) | Comments | mp$^a$ (°C.) |
|---|---|---|---|---|
| 58 | MeOSuc—Ala—Ala—Pro—CH$_2$—N(iPr)—CO—O—C$_6$F$_4$—F (pentafluorophenyl) | 37.5 | + | 152–154 |

TABLE 3-continued

Peptidyl Carbamates (ROCONR'R") where R'R"N is a polypeptide
Effect of Variations in $P_5$ and $P_3$ on inhibitory activity towards PP elastase

| Compound No. | Structure | Ki (μM) | Comments | mp[a] (°C.) |
|---|---|---|---|---|
| 93 | CF$_3$CO—Ala—Ala—Pro—CH$_2$—N(iPr)—CO—O—(pentafluorophenyl) | 49.0 | + | 85-88 |

+ AT LEAST 95% INHIBITION OF PP ELASTASE OBSERVED IN 30 MIN AT $\frac{[I]}{[E]}$ = 260, [I] ~ 150 μM

[a] ALL COMPOUNDS WERE NOVEL AND WERE IDENTIFIED BY SPECTRAL DATA AND ELEMENTAL ANALYSIS.

TABLE 4

Peptidyl Carbamates: Relative inhibitory activity towards PP and HL elastase.

| No= | $P_6$ | $P_5$ | $P_4$ | $P_3$ | $P_2$ | $P_1$ | $P_1'$ | PPE[(1)] | HLE[(2)] |
|---|---|---|---|---|---|---|---|---|---|
| 18 | | MeO—Suc—Ala—Ala—Pro—CH$_2$—N(iPr)—C(=O)—S— | | | | | 1-methyltetrazol-5-yl (via CH) | + | + |
| 22 | | MeO—Suc—Ala—Ala—Pro—CH$_2$—N(cyclopropyl)—C(=O)—S— | | | | | 1-methyltetrazol-5-yl | − | + |
| 26 | | MeO—Suc—Ala—Ala—Pro—CH$_2$—N(Et)—C(=O)—S— | | | | | 1-methyltetrazol-5-yl | + | + |
| 36 | | MeO—Suc—Ala—Ala—Pro—CH$_2$—N(n-Bu)—C(=O)—S— | | | | | 1-methyltetrazol-5-yl | + | + |
| 39 | | MeO—Suc—Ala—Ala—Pro—CH$_2$—N(iPr)—C(=O)—S— | | | | | 1-phenyltetrazol-5-yl | + | + |
| 43 | | MeO—Suc—Ala—Ala—Pro—CH$_2$—N(allyl)—C(=O)—S— | | | | | 1-methyltetrazol-5-yl | + | + |
| 47 | | MeO—Suc—Ala—Ala—Pro—CH$_2$—N(iPr)—C(=O)—O—C$_6$H$_4$—NO$_2$ | | | | | | − | * |

TABLE 4-continued

Peptidyl Carbamates: Relative inhibitory activity towards PP and HL elastase.

| No= | P6 | P5 | P4 | P3 | P2 | P1 | P1' | PPE[1] | HLE[2] |
|---|---|---|---|---|---|---|---|---|---|
| 51 | | MeO—Suc—Ala—Ala—Pro—CH$_2$—N(CH$_2$Ph)—C(=O)—O—C$_6$H$_4$—NO$_2$ | | | | | | — | — |
| 55 | | MeO—Suc—Ala—Ala—Pro—CH$_2$—N(cyclohexyl)—C(=O)—O—C$_6$H$_4$—NO$_2$ | | | | | | — | — |

[1] 39 > 26 > 18 = 43 > 36 > 22
[2] 39 > 43 = 18 > 26 > 22 = 36
— No inhibition at [I] < 150 μM using [E] = 0.61 μM.
\* Not tested for HLE As will be apparent from the above tables, the useful peptidyl carbamates of the invention were found to exhibit specific inhibition of porcine pancreatic elastase without affecting the other two enzymes. The rate and extent of inhibition could be effected by varying the structure of R and R'. As shown from kinetic parameters when R is p-nitrophenol, and R' was varied, all the peptidyl carbamates inhibited PP elastase except when R' was a tert-butyl group. As shown in Table 4, when R' is cyclohexyl and benzyl, the compounds are also inactive. In all cases the inhibition was specific and competitive. When R' was kept as an isopropyl group and R varied, it was found that when R is an aromatic alcohol or thio-heterocycle with good nucleofugicity, the peptidyl carbamates were specific inhibitors of elastase. However, when R was an aliphatic alcohol or thioalcohol it was found that polyhalogenated groups give better inhibitors than simple hydrocarbons. When compounds where the extended chain was shortened into two amino acids, were tested against the serine proteases, it was found that the inhibitory activity of the carbamates disappeared. Moreover, the nature of the protecting group (P$_5$) seemed to affect the affinity of the inhibitor for the enzyme. In all these cases the inhibition was studied at different substrate and inhibitor concentrations and the mode of inhibition determined from Lineweaver-Burk and Dixon plots. Ki values were calculated from the latter. Active peptidyl carbamate inhibitors were found to have a Ki value ranging from 49 μM to 14.8 μM. The Km value for the substrate used (BOC-Ala-ONp) was 4800 μM. The enzymatic activity of PP elastase after treatment with the inhibitor(s) was also tested using the natural substrate elastin-congo red.

In contrast to chloromethyl ketone inhibitors, the carbamate esters of the invention do not inhibit the enzyme permanently as evidenced by the recovery of enzymatic activity of PP elastase in 72 h after inhibition. This reversibility of inhibition, along with the hydrolysis of 6 by PP elastase (as detected by the release of p-nitrophenol) support the mechanism of inhibition proposed herein.

The following abbreviations are used in this specification:

BOC=t-Butyloxy carbonyl, Ala=L-alanine, Pro=L-proline, Val=L-valine, ONp=p-nitrophenol, PP=porcine pancreatic, HL=human leukocyte. All amino acids used herein are L-amino acids.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the following general formula:

$$Z-Ala-Ala-Pro-CH_2-\underset{R'}{N}-\overset{O}{\overset{\|}{C}}-XR$$

wherein Z is selected from the group consisting of R"O—Suc— where R" is lower alkyl of 1 to 3 carbon atoms and CF$_3$CO—; X is oxygen or sulfur; R' is selected from the group consisting of straight or secondary branch-chained alkyl of 1 to 4 carbon atoms, alkenyl of 2 to 3 carbon atoms, alkynyl of 2 to 4 carbon atoms, cycloalkyl of 3 to 6 carbon atoms, and benzyl, and R is selected from the group consisting of substituted or unsubstituted phenyl wherein the substituents are selected from the group consisting of nitro, and pentafluoro; benzyl, CH$_2$CF$_2$CF$_2$CF$_3$, 1-lower alkyl tetrazolyl, 1-phenyltetrazolyl, 2-thioxo-3-thiazolidinyl-, pyridyl and benzothiazolyl, provided that when R is paranitrophenyl, R' is other than tertiary-butyl, benzyl or cyclohexyl, and when X is sulfur, R is other than benzyl.

2. A compound according to claim 1 wherein Z is CH$_3$O—Suc—.

3. A compound according to claim 1 wherein R' is selected from the group consisting of —CH(CH$_3$)$_2$, —CH$_2$CH$_2$CH$_3$, —CH$_3$, —C(CH$_3$)$_3$, cyclopropyl, cyclohexyl, and benzyl.

4. A compound according to claim 1 wherein R is para-nitrophenyl.

5. A compound according to claim 1 wherein R is phenyl.

6. A compound according to claim 1 wherein R is perfluorophenyl.

7. A compound according to claim 1 wherein R is —OCH$_2$CF$_2$CF$_2$CF$_3$.

8. A compound according to claim 1 wherein R is 1-lower alkyltetrazolyl or 1-phenyltetrazolyl.

9. A compound according to claim 1 wherein R is pyridyl.

10. A compound according to claim 1 wherein R is 2-thioxo-3-thiazolidinyl.

11. A compound according to claim 1 wherein R is benzothiazolyl.

12. A compound according to claim 1 wherein Z is CH₃OSuc—, R' is —CH(CH₃)₂, and R is 1-methyltetrazolyl.

13. A compound of the following general formula:

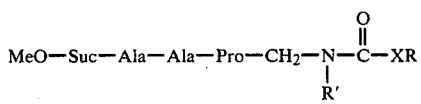

wherein X is O or S and wherein R is selected from the group consisting of phenyl, nitrophenyl, fluorophenyl, —CH₂CF₂CF₂CF₃, 1-lower alkyltetrazolyl, 1-phenyltetrazolyl, benzyl, 2-thioxo-3-thiazolidinyl, pyridyl, and benzothiazolyl, and R' is selected from the group consisting of straight or secondary branch-chained alkyl of 1 to 4 carbons, alkenyl of 2 to 3 carbon atoms, alkynl of 2 to 4 carbon atoms, cycloalkyl of 3 to 6 carbon atoms, and benzyl, provided that when R is p-nitrophenyl, R' is other than tertiary-butyl, benzyl or cyclohexyl, and when X is sulfur R is other then benzyl.

14. A compound according to claim 12 wherein R is p-nitrophenyl and R' is isopropyl.

15. A compound according to claim 13 wherein R is 1-methyltetrazolyl, and R' is isopropyl.

16. A compound of the formula:

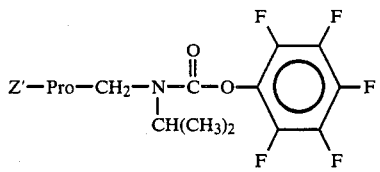

wherein Z' is selected from the group consisting of MeO—Suc—Ala—Ala and CF₃CO—Ala—Ala.

17. A compound according to claim 1 selected from the group consisting of:

p-Nitrophenyl N-(Methyl succinyl-L-alanyl-L-alanyl-L-prolylmethyl)-N-isopropyl carbamate;

Phenyl N-(Methyl Succinyl-L-Alanyl-L-Alanyl-L-Prolyl Methyl)-N-Isopropyl Carbamate;

Pentafluorophenyl N-(methyl succinyl-L-alanyl-L-alanyl-L-prolymethyl)-N-isopropyl-carbamate;

Heptafluorobutyl N-(methyl succinyl-L-alanyl-L-alanyl-L-prolylmethyl) N-isopropylcarbamate;

1-Methyl-5-tetrazolyl N-(methyl succinyl-L-alanyl-L-alanyl-L-prolylmethyl)-N-isopropylthiocarbamate;

P-Nitrophenyl N-(Methyl succinyl-L-alanyl-L-alanyl-L-propylmethyl) N-propylcarbamate;

P-Nitrophenyl N-(methyl succinyl-L-alanyl-L-alanyl-L-prolylmethyl)-N-cyclopropylcarbamate;

p-Nitrophenyl-N-(Methyl succinyl-L-alanyl-L-alanyl-L-prolylmethyl)-N-methyl-carbamate;

Pentafluorophenyl N-(trifluoroacetyl-L-alanyl-L-alanyl-L-prolylmethyl)-N-isopropylcarbamate;

1-Methyl-5-tetrazolyl N-(methyl succinyl-L-alanyl-L-alanyl-L-prolylmethyl)-N-cyclopropylthiocarbamate;

1-Methyl-5-tetrazolyl N-(methyl succinyl-L-alanyl-L-alanyl-L-prolylmethyl)-N-propylthiocarbamate.

1-Methyl-5-tetrazolyl N-(methyl succinyl-L-alanyl-L-alanyl-L-propylmethyl)-N-butylthiocarbamate;

1-Phenyl-5-tetrazolyl N-(methyl succinyl-L-alanyl-L-alanyl-L-prolylmethyl)-N-isopropylthiol carbamate; and 1-Methyl-5-tetrazolyl N-(methyl succinyl-L-alanyl-L-alanyl-L-prolylmethyl)-N-allylthiocarbamate.

18. Elastase inhibitor compositions comprising a carrier, and an elastase inhibiting-effective amount of an effective compound of the following formula:

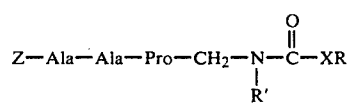

wherein Z is selected from the group consisting of R″O—Suc— where R″ is lower alkyl of 1 to 3 carbon atoms and CF₃CO—; X is oxygen or sulfur; R' is selected from the group consisting of straight or secondary branch-chained alkyl of 1 to 4 carbon atoms, alkenyl of 2 to 3 carbon atoms, alkynyl of 2 to 4 carbon atoms, cycloalkyl of 3 to 6 carbon atoms, and benzyl, and R is selected from the group consisting of substituted or unsubstituted phenyl wherein the substituents are selected from the group consisting of nitro, and pentafluoro; benzyl, CH₂CF₂CF₂CF₃, 1-lower alkyl tetrazolyl, 1-phenyltetrazolyl, 2-thioxo-3-thiazolidinyl-, pyridyl and benzothiazolyl, provided that when R is paranitrophenyl, R' is other than tertiary-butyl, benzyl or cyclohexyl, and when X is sulfur, R is other than benzyl.

19. A composition according to claim 20 wherein Z is CH₃O—Suc— and wherein R' is selected from the group consisting of —CH(CH₃)₂, —CH₂CH₂CH₃, —CH₃, —C(CH₃)₃, cyclopropyl, cyclohexyl, and benzyl.

20. A composition according to claim 19 wherein R is selected from the group consisting of para-nitrophenoyl, perfluorophenyl, OCH₂CF₂CF₂CH₃, 1-methyltetrazolyl, 1-phenyltetrazolyl, 2-thioxo-3-thiazolidinyl, pyridyl and benzothiazolyl.

21. A composition according to claim 18 wherein Z is CH₃OSuc—, R' is isopropyl, and R is 1-methyltetrazolyl.

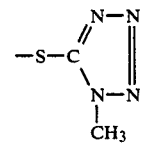

22. A composition according to claim 18 wherein the composition contains an elastase-inhibiting amount of a compound of the formula:

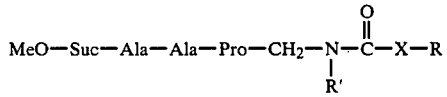

wherein X is oxygen or sulfur, R is selected from the group consisting of phenyl, p-nitrophenyl, pentafluorophenyl, —O—CH₂CF₂CF₂CF₃, 1-methyltetrazolyl, 1-phenyltetrazolyl, 2-thioxo-3-thiazolidinyl, pyridyl, benzyl and benzothiazolyl, and R' is selected from the group consisting of lower alkyl, lower alkenyl, lower alkynl, and benzyl, provided that when R is p- nitrophenyl, R' is other than tert-butyl, and when X is sulfur R is other than benzyl.

23. A composition according to claim 22 wherein R is p-nitrophenyl and R' is isopropyl.

24. A composition according to claim 22 wherein R is 1-methyl or 1-phenyltetrazolyl, and R' is isopropyl.

25. A composition according to claim 18 wherein the composition contains an elastase-inhibiting amount of a compound of the formula:

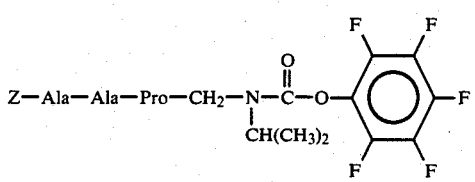

wherein Z is as defined in claim 18.

26. A composition according to claim 18 wherein the effective compound is selected from the group consisting of:
p-Nitrophenyl N-Methyl succinyl-L-alanyl-L-alanyl-L-prolylmethyl)-N-isopropyl carbamate;
Phenyl N-(Methyl Succinyl-L-Alanyl-L-Alanyl-L-Prolyl Methyl)-N-Isopropyl Carbamate;
Pentafluorophenyl N-(methylsuccinyl-L-alanyl-L-alanyl-L-prolymethyl)-N-isopropyl-carbamate;
Heptafluorobutyl N-(methyl succinyl-L-alanyl-L-alanyl-L-prolylmethyl) N-isopropylcarbamate;
1-Methyl-5-tetrazolyl N-(methyl succinyl-L-alanyl-L-alanyl-L-prolylmethyl)-N-isopropylthiocarbamate;
P-Nitrophenyl N-(Methyl succinyl-L-alanyl-L-prolylmethyl) N-propylcarbamate;
P-Nitrophenyl N-(methyl succinyl-L-alanyl-L-alanyl-L-prolylmethyl)-N-cyclopropylcarbamate;
p-Nitrophenyl-N-(Methyl succinyl-L-alanyl-L-alanyl-L-prolylmethyl)-N-methyl-carbamate;
Pentafluorophenyl N-(trifluoroacetyl-L-alanyl-L-alanyl-L-prolylmethyl)-N-isopropylcarbamate;
1-Methyl-5-tetrazolyl N-methyl succinyl-L-alanyl-L-alanyl-L-prolylmethyl)-N-cyclopropylthiocarbamate;
1-Methyl-5-tetrazolyl N-(methyl succinyl-L-alanyl-L-alanyl-L-prolylmethyl)-N-propylthiocarbamate.
1-Methyl-5-tetrazolyl N-(methyl succinyl-L-alanyl-L-alanyl-L-propylmethyl)-N-butylthiocarbamate;
1-Phenyl-5-tetrazolyl N-(methyl succinyl-L-alanyl-L-alanyl-L-prolylmethyl)-N-isopropylthio carbamate; and
1-Methyl-5-tetrazolyl N-(methyl succinyl-L-alanyl-L-alanyl-L-prolylmethyl)-N-allylthiocarbamate.

27. A composition according to claim 18 wherein the effective ingredient is present in a concentration of about 0.001 to 2.0 weight percent in an inert carrier or adjuvent.

28. A method for inhibiting the enzyme elastase in animals and humans which comprises administration thereto of a composition of claim 18.

29. A method for inhibiting the enzyme elastase in animals and humans which comprises administration thereof of a composition of claim 22.

30. A method for inhibiting the enzyme elastase in animals and humans which comprises administration thereto of a composition of claim 26.

* * * * *